(12) United States Patent
Okumura et al.

(10) Patent No.: US 7,280,202 B2
(45) Date of Patent: Oct. 9, 2007

(54) INGREDIENT ANALYSIS METHOD AND INGREDIENT ANALYSIS APPARATUS

(75) Inventors: Tomohiro Okumura, Kadoma (JP); Mitsuo Saitoh, Neyagawa (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 403 days.

(21) Appl. No.: 11/032,803

(22) Filed: Jan. 10, 2005

(65) Prior Publication Data

US 2005/0162647 A1    Jul. 28, 2005

(30) Foreign Application Priority Data

Jan. 15, 2004  (JP) .............................. 2004-007698

(51) Int. Cl.
*G01J 3/30* (2006.01)
*G01N 15/04* (2006.01)

(52) U.S. Cl. ...................... 356/316; 356/317; 356/313; 356/314; 356/417; 209/576; 209/582

(58) Field of Classification Search ................ 356/316, 356/317, 313, 314, 417; 209/576, 582
See application file for complete search history.

(56) References Cited

FOREIGN PATENT DOCUMENTS

| JP | 10-267868 | 10/1998 |
|----|-----------|---------|
| JP | 2000-258347 | 9/2000 |
| JP | 2000-269614 | 9/2000 |
| JP | 2002-310952 | 10/2002 |

*Primary Examiner*—Gregory J. Toatley, Jr.
*Assistant Examiner*—Abdullahi Nur
(74) *Attorney, Agent, or Firm*—Pearne & Gordon LLP

(57) ABSTRACT

In an ingredient analysis method and an ingredient analysis apparatus in accordance with the present invention, high-frequency power is supplied from a power source 4 while helium gas is supplied to an atmospheric pressure plasma source 2 disposed near a substance to be analyzed, whereby plasma 5 is generated, and the substance to be analyzed is exposed to the plasma 5 and emits light. The light is guided to a filter 7 and a photodiode 8 via an optical fiber 6 and subjected to photoelectrical conversion. The signal obtained by the photoelectrical conversion is sent to a controller 9. The controller 9 judges whether a specific element is present or not in the substance to be analyzed.

20 Claims, 17 Drawing Sheets

INGREDIENT ANALYSIS METHOD AND INGREDIENT ANALYSIS APPARATUS

BACKGROUND OF THE INVENTION

The present invention relates to an ingredient analysis method and an ingredient analysis apparatus for analyzing the ingredients of a substance.

In general circuit boards for use in electrical and electronic products, various circuit components mounted on printed-circuit boards and film circuit boards are connected by using solder. As solder for connecting these circuit components on circuit boards, tin-lead eutectic solder containing a large amount of lead has conventionally been used widely to ensure workability and product reliability.

However, in the case when used electrical and electronic products including circuit boards on which this kind of lead-containing solder is used are left out of doors as waste or dumped for landfill, groundwater is contaminated with lead melted from the waste and then mixed into drinking water. Hence, there is a fear of adversely affecting the human body. Therefore, such electrical and electronic products including circuit boards on which this kind of lead-containing solder is used are dumped for landfill at controlled landfill sites being controlled so that contaminated water containing lead does not leak.

In order that environmental contamination is prevented more securely, it is preferable that used electrical and electronic products are dismantled and separated, and circuit boards are retrieved, and then lead is separated and recovered from the circuit boards. However, the separation and recovery of lead requires time and effort, and as a result, considerably high cost for separation and recovery is involved in the resultant recycled lead.

Furthermore, in recent years, a chemical recovery method has been used wherein used electrical and electronic products are dismantled, circuit boards to be disposed (hereinafter referred to as waste circuit boards) are retrieved therefrom and crushed, and the crushed pieces obtained in it is dry distilled and recovered. With this chemical recovery method, recycling has begun to be used to recover relatively expensive metals (valuable metals), such as gold, silver, copper and palladium, being used as wiring and plating materials. In this case, silicides, such as glass, usually contained in waste circuit boards are recovered as slag. This slag can be effectively recycled as a cement material or the like. However, in the case that the waste circuit boards contain lead, the lead is mixed into the slag. Hence, in order that this slag is effectively utilized as a cement material or the like, the lead is required to be separated and recovered. However, at present, this kind of slag containing lead is not recycled but dumped for landfill at controlled landfill sites because of the cost for lead separation and recovery.

Therefore, in recent years, in order that environmental contamination can be prevented more securely and that recycling can be performed easy, it is desired that tin-lead eutectic solder is switched to solder not containing lead so-called lead-free solder. Therefore, circuit board manufacturing companies are energetically advancing the switching from tin-lead eutectic solder to lead-free solder. When waste circuit boards on which lead-free solder is used are crushed and dry distilled, valuable metals can be recovered and slag not including lead can also be recovered. Therefore, the recovered slag can be utilized effectively as a cement material or the like.

However, lead-free solder being known at present and used practically has a melting point higher than that of tin-lead eutectic solder. For example, Sn—Ag—Cu lead-free solder, being most prospective as lead-free solder at present, has a melting point of 216 to 220° C.; and tin-lead eutectic solder has a melting point of approximately 183° C. Since the lead-free solder has higher melting points, soldering is required to be carried out at higher temperatures. Hence, some circuit components have a problem in thermal resistance against such high soldering temperatures, even though they have thermal resistance against conventional soldering temperatures. In addition, circuit components are occasionally required to be checked individually by reliability tests after soldering, depending on the material and shape of the leads in the circuit components.

Therefore, it is difficult to completely replace solder included in circuit boards and products comprising such circuit boards with lead-free solder. Hence, lead-containing solder is still used for some circuit boards. Moreover, there exist numerous products that use lead-containing solder among electrical and electronic products having already been produced and used. Hence, it is inevitable situation that circuit boards on which lead-containing solder is used and circuit boards on which lead-free solder is used are mixed up at worksites where used electrical and electronic products are dismantled and separated and then circuit boards are retrieved.

If there is no effective means for separating waste circuit boards on which lead-free solder is used, recycling and waste dumping are carried out in a state wherein circuit boards on which lead-containing solder is used and circuit boards on which lead-free solder is used are mixed up. This results in causing some problems described below.

First, if only the waste circuit boards on which lead-free solder is used are present, slag obtained by crushing and dry distilling the waste circuit boards can be utilized effectively as a cement material or the like, for example. However, if some circuit boards on which lead-containing solder is used are mixed into waste circuit boards on which lead-free solder is used, lead is mixed into the slag, and the slag cannot be utilized effectively as a cement material or the like. Hence, even the circuit boards on which lead-free solder is used with much effort have no option but to be dumped for landfill at controlled landfill sites together with the waste circuit boards on which lead-containing solder is used, after valuable metals are recovered.

Furthermore, if lead-free solder is mixed into lead-containing solder when lead is recovered from slag obtained by crushing, dry distilling waste circuit boards, and recovering valuable metals, the content of lead is reduced, and the cost for lead separation and recovery becomes rather higher.

For the above-mentioned reasons, it is desired that a method capable of separating lead-containing boards from lead-free boards easily at low cost is realized.

Since both the lead-containing solder and the lead-free solder primarily consist of tin, they have a slight difference in luster; however, it is difficult to distinguish them visually.

Hence, a method for separating circuit-board including lead-containing solder from circuit-board including lead-free solder, by providing identification marks, bar codes or the like has been disclosed in the Official Gazette of Unexamined Japanese Patent Publication No. 2000-269614, for example.

However, in the separation method using identification marks, bar codes or the like, it occurs occasionally that space for the identification marks, bar codes or the like cannot be obtained on the circuit boards of electrical and electronic products being required to be reduced in size, thickness and weight. In addition, it may be assumed occasionally that the identification marks, bar codes or the like are reduced in size and become difficult to identify. Furthermore, it is necessary to add a step for providing the identification marks, bar codes or the like in a circuit board manufacturing process, thereby causing a problem of manufacturing cost increase.

Moreover, in the work of dismantling and separating used electrical and electronic products and retrieving circuit boards, various products and circuit boards made by numerous manufacturing companies are mixed up. Therefore, in the separation method disclosed in the Official Gazette of Unexamined Japanese Patent Publication No. 2000-269614, it is essential that the identification marks, bar codes or the like should be standardized. However, this standardization cannot be attained easily. The method is thus not a secure method that can be attained promptly.

Still further, the terminal wires of numerous circuit components are plated with lead-containing solder even though the circuit components themselves are soldered with lead-free solder. It is realistically impossible that the lead-containing solder on all of these terminal wires is replaced with lead-free solder at a certain time simultaneously. Hence, it is likely that circuit components plated with lead-containing solder and circuit components plated with lead-free solder are mixed up inevitably. However, it is realistically impossible to represent these by using only the identification marks, bar codes or the like.

Still further, in addition to the problem of lead, waste circuit boards have a problem regarding bromine that is in danger of generating dioxin in the stage of waste incineration.

Insulating materials primarily consisting of synthetic resin are usually used for printed-circuit boards on which circuit components are mounted. Generally speaking, most of these insulating materials contain flame retardants based on halogen (including bromine), i.e., brominated diphenyl ether compounds, brominated biphenyl compounds, etc., so as to satisfy the flame retardation requirements specified in standards for safety during usage, for example, the UL Standards (Unites States Safety Standards). When circuit boards are incinerated as waste, such flame retardants based on halogen (including bromine) are in danger of generating dioxin during imperfect combustion. Therefore, such circuit boards containing bromine are required to be dumped for landfill without being incinerated or required to be incinerated under strict combustion control conditions so as not to generate dioxin.

Recently, the development of halogen-free printed-circuit boards, not containing bromine, has been proceeded. These printed-circuit boards have no danger of generating dioxin.

However, halogen-based flame retardants are used in numerous electrical and electronic products having already been produced and used. Hence, it is inevitable that circuit boards in which flame retardants based on halogen (including bromine) are used and halogen-free circuit boards are mixed up at worksites where used electrical and electronic products are dismantled and separated and then circuit boards are retrieved.

If circuit boards in which flame retardants in which flame retardants based on halogen (including bromine) are used are mixed into halogen-free circuit boards, there is in danger of generating dioxin during incineration. Furthermore, if processing not generating dioxin is carried out, processing cost increases.

Therefore, in order that the generation of dioxin is prevented and that processing cost is reduced, it is desired that circuit boards containing bromine and circuit boards not containing bromine are separated and then dumped at the stage of dumping circuit boards.

As a conventional method for separating waste, a separation method using fluorescent X-rays is known. For example, a material identification apparatus wherein waste is irradiated with primary X-rays and identified on the basis of characteristic X-rays generated therefrom is proposed in the Official Gazette of Unexamined Japanese Patent Publication No. Hei 10-267868. Furthermore, the Official Gazette of Unexamined Japanese Patent Publication No. 2002-310952 proposes a method wherein the surface of a waste circuit board is analyzed with a fluorescent X-ray analyzer, a judgment as to whether lead is present or not is made on the basis of the result of the analysis. The separation between a waste circuit board containing lead and a waste circuit board not containing specific elements on the surfaces is thus carried out according to the judgment. These conventional apparatuses are large-size apparatuses for analyzing and identifying waste materials on belt conveyors in a hermetically closed room.

The Official Gazette of Unexamined Japanese Patent Publication No. 2000-258347 discloses ICP (Inductively Coupled Plasma) emission spectrometry technology. In this emission spectrometry technology, a solder sample serving as an analysis object is prepared. Plasma is generated by passing a carrier gas in which the prepared solder sample is mixed through a pipe and by passing a high-frequency current in the coil wound outside the pipe, whereby light is emitted from the sample to carry out spectroscopic analysis.

However, the conventional analysis technologies have problems. For example, the procedure for analysis operation is complicated and takes a long period of time for analysis, and expensive analysis instruments are required. In addition, since vacuum processing is required for analysis, there is a problem of requiring a sturdy vacuum vessel and a pump.

DISCLOSURE OF THE INVENTION

In consideration of the problems encountered in the above-mentioned conventional technologies, the present invention is intended to provide an ingredient analysis method and an ingredient analysis apparatus capable of simplifying the procedure for analysis operation, carrying out analysis in a short period of time and attaining analysis at low cost.

In order to attain the above-mentioned object, an ingredient analysis method in accordance with the present invention comprises the steps of:

setting the relationship between a wavelength and the emission intensity thereof obtained when plasma is applied to a specific element at atmospheric pressure;

selecting a specific wavelength having a peak value of the emission intensity on the basis of the relationship set in said step of setting;

applying said plasma to a substance to be analyzed at atmospheric pressure and measuring the emission intensity of said substance to be analyzed at said wavelength selected in said step of selecting; and comparing the emission intensity measured in said step of measuring and the emission intensity at said wavelength of said step of setting and judging the presence or absence of said element in said substance to be analyzed.

With the ingredient analysis method in accordance with the present invention having the above-mentioned processing steps, it is possible to attain analysis that can be carried out according to simple operation procedures in a short time at low cost. Furthermore, with the ingredient analysis method in accordance with the present invention, printed-circuit boards can be separated easily and securely.

In order to attain the above-mentioned object, an ingredient analysis apparatus in accordance with the present invention comprises a sample table on which a substance to be analyzed is placed, a discharge electrode having a gas passage formed therein, a gas supplying section for supplying gas to the above-mentioned discharge electrode, power source for supplying power to the above-mentioned discharge electrode, a light transmission section, formed of a light transmission material and having an emission input section disposed near plasma generated between the above-mentioned discharge electrode and the above-mentioned substance to be analyzed, for transmitting light from the above-mentioned substance to be analyzed, the above-mentioned light being generated by plasma irradiation, a filter for allowing only the light having a specific wavelength in the light from the above-mentioned light transmission section to passes through, and a controller for measuring the emission intensity of the light having passed through the above-mentioned filter and for judging the presence or absence of a specific element in the above-mentioned substance to be analyzed.

With the ingredient analysis method in accordance with the present invention configured as described above, it is possible to attain analysis that can be carried out according to simple operation procedures in a short time at low cost.

It will be recognized that some or all of the figures are schematic representations for purposes of illustration and do not necessarily depict the actual relative sizes or locations of the elements shown.

BEST MODES FOR CARRYING OUT THE INVENTION

Preferred embodiments of an ingredient analysis method in accordance with the present invention and an ingredient analysis apparatus using the ingredient analysis method will be described below referring to the accompanying drawings.

First Embodiment

A first embodiment in accordance with the present invention will be described below referring to FIG. 1 to FIG. 5.

Figure 1:
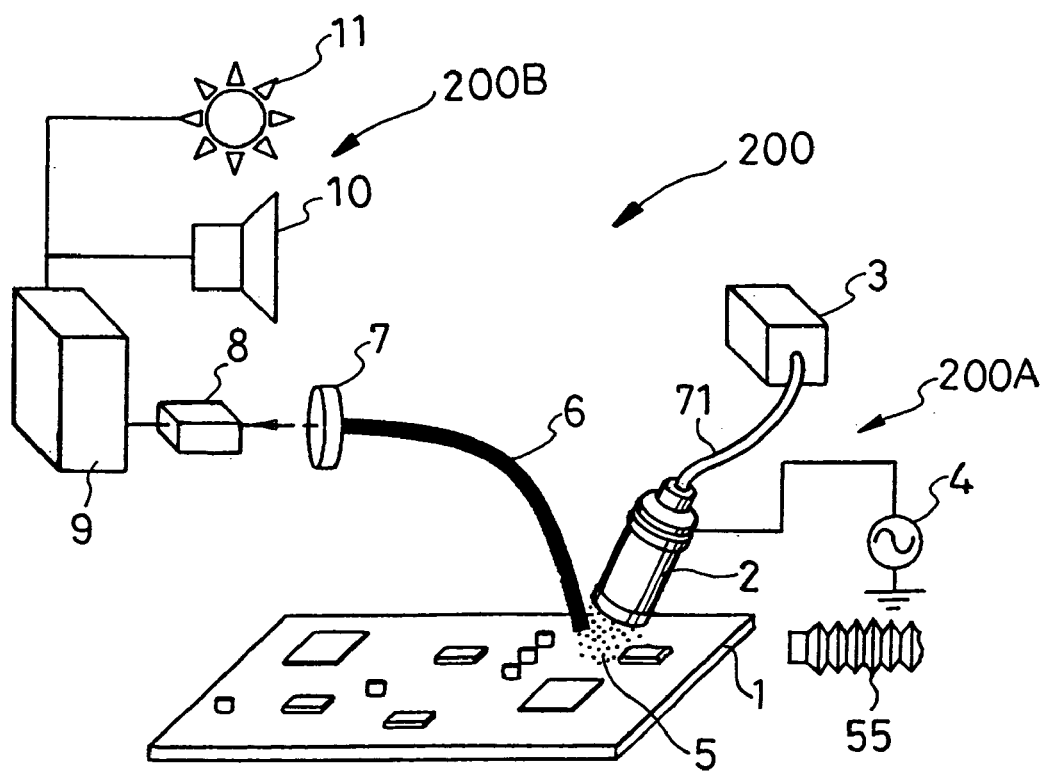
FIG. 1 is a view showing a schematic configuration of a first ingredient analysis apparatus in accordance with a first embodiment of the present invention.
Figure 2A:
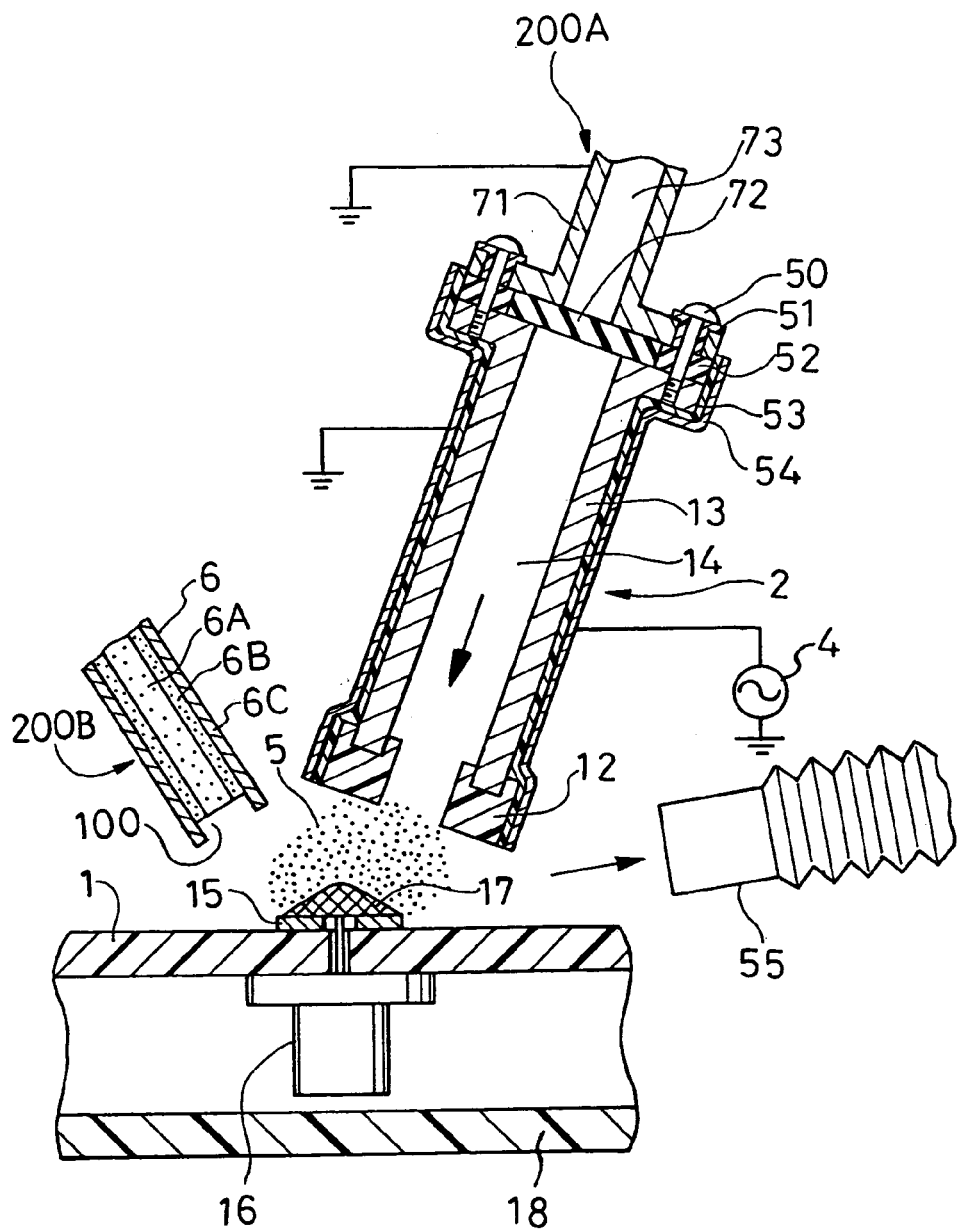
FIG. 2A is an enlarged cross-sectional view showing a portion for generating plasma of the first ingredient analysis apparatus in accordance with the first embodiment of the present invention.

FIG. 1 is a schematic view showing a first ingredient analysis apparatus in accordance with the first embodiment of the present invention. FIG. 2A is an enlarged cross-sectional view showing a portion for generating plasma of the first ingredient analysis apparatus in accordance with the first embodiment of the present invention. In the first embodiment, a case wherein an object to be inspected is a printed circuit board will be described; however, the object to be inspected may be a film circuit board.

FIG. 1 is a view showing a state in which a waste printed-circuit board 1 serving as an object to be inspected is inspected by the first ingredient analysis apparatus 200 in accordance with the first embodiment for ingredient analysis of solder. As shown in FIG. 1, the first ingredient analysis apparatus 200 includes a plasma generating part 200A for generating plasma and an ingredient analyzing part 200B for accepting plasma to analyze the ingredients thereof. The plasma generating part 200A comprises an atmospheric pressure plasma source 2, a gas supplying device 3, power source 4, and an exhaust device 55. The ingredient analyzing part 200B comprises a light transmission part 6, a filter 7, a photodiode 8, a controller 9, a speaker 10, an indicator 11. The first embodiment is configured so that plasma is generated at atmospheric pressure, wherein the atmospheric pressure is 0.8 atmosphere to 1.2 atmosphere (atm). The conditions of the atmospheric pressure are the same in the following embodiments.

Figure 2B:
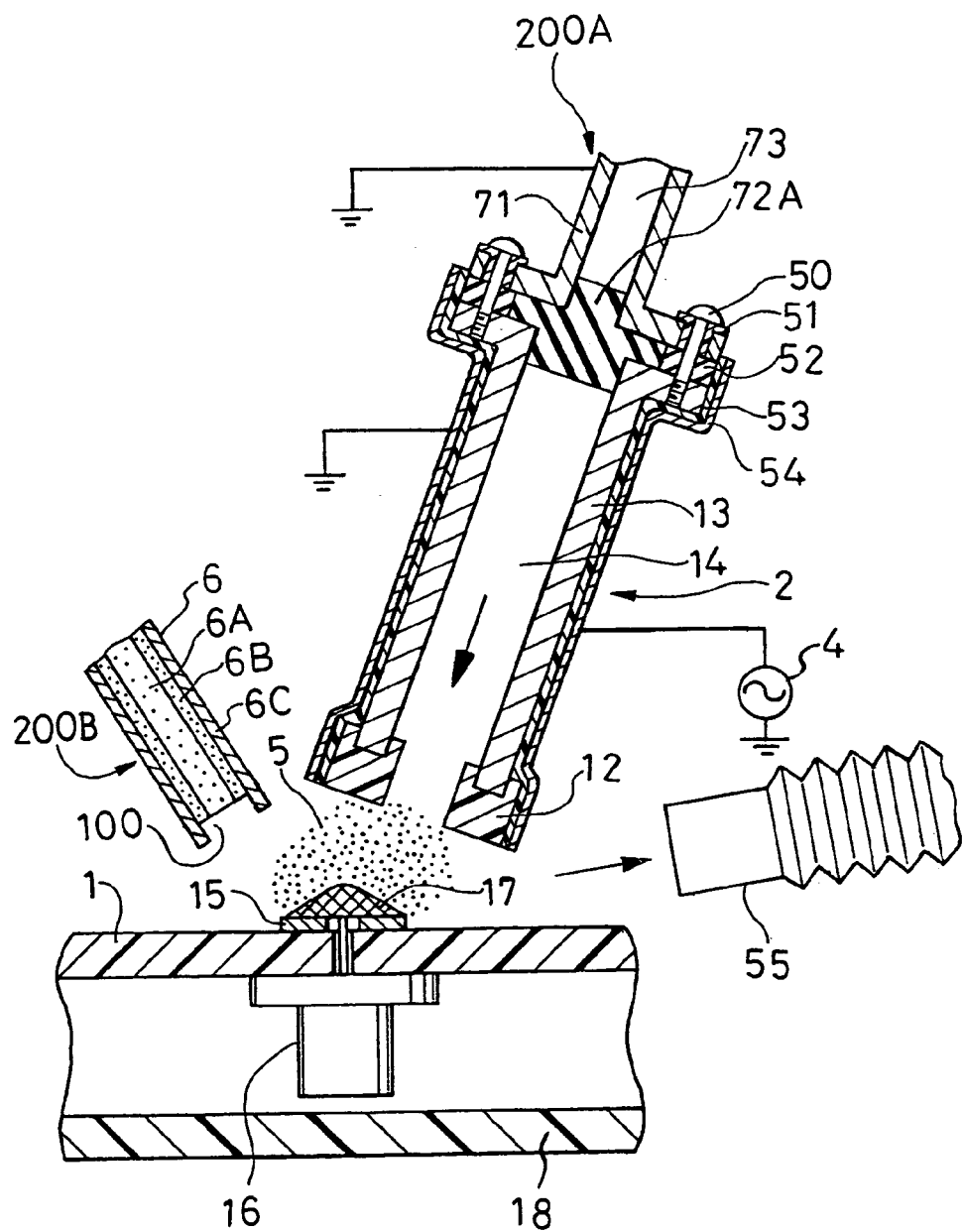
FIG. 2B is an enlarged cross-sectional view showing another configuration of the first ingredient analysis apparatus in accordance with the first embodiment of the present invention.

As shown in FIG. 2A, the atmospheric pressure plasma source 2 of the plasma generating part 200A is internally provided with a gas passage 14, and comprises a discharge electrode 13 having a substantially cylindrical shape, a dielectric substance 12 covering the tip of the discharge electrode 13, an insulator 53 covering the peripheral face of the discharge electrode 13, and a cover 54 made of metal covering the insulator 53. The atmospheric pressure plasma source 2 and the gas supplying device 3 are connected via a stainless steel pipe 71 so that a gas passage 73 communicates the gas passage 14 in the atmospheric pressure plasma source 2. The discharge electrode 13 of the atmospheric pressure plasma source 2 and the stainless steel pipe 71 are joined with bolts 50 via insulating materials. The bolt 50 is screwed in the discharge electrode 13 through a ceramic bush 51 attached to the flange of the stainless steel pipe 71 and a ceramic ring 52 placed between the flange of the stainless steel pipe 71 and the flange of the discharge electrode 13. In the center portion of the ceramic ring 52, a porous ceramic 72 which is porous and permeable to air is provided. Since the porous ceramic 72 is provided as mentioned above, the atmospheric pressure plasma source 2 has an effect of preventing discharge in the piping. As a result, the flange of the stainless steel pipe 71 and the flange of the discharge electrode 13 are firmly joined in an insulated state. In the first embodiment, alumina ($Al_2O_3$) is used as a material for the ceramic ring 52 and the porous ceramic 72. The ceramic ring 52 and the porous ceramic 72 may use other ceramics as a material thereof, and may be formed of, for example, zirconia ($ZrO_2$), aluminium nitride (AlN), silicon nitride (SiN), and silicon carbide (SiC). As a configuration for further improving the effect of preventing discharge in the piping in the vicinity of the joint of the atmospheric pressure plasma source 2 and the stainless steel pipe 71, there is a configuration shown in FIG. 2B. The configuration shown in FIG. 2B differs from that shown in FIG. 2A in the shape of a porous ceramic 72A. As shown in FIG. 2B, one end of the porous ceramic 72A having porosity and air permeability disposed in the center portion of the ceramic ring 52 protrudes in the discharge electrode 13. The other end of the porous ceramic 72A protrudes in the stainless steel pipe 71. The porous ceramic 72 configured as mentioned above has an excellent effect of preventing discharge in the piping in the vicinity of the joint.

The discharge electrode 13 of the atmospheric pressure plasma source 2 is connected to the power source 4, and is supplied with high-frequency power. On the other hand, the cover 54 as a sheath of the atmospheric pressure plasma source 2 is grounded, and the stainless pipe 71 is grounded. Therefore, the atmospheric pressure plasma source 2 has an excellent operability that an inspector can operate the atmospheric pressure plasma source 2 manually with respect to the printed-circuit board 1 serving as an object to be inspected, and thereby locating it at a desirous position with respect to the printed-circuit board 1.

As shown in FIG. 2A, the light transmission part 6 in the ingredient analyzing part 200B comprises an optical fiber 6A, a buffer coating layer 6B covering the peripheral face thereof, and a cover 6C made of metal. The light transmission part 6 configured as mentioned above has flexibility, and is manually positioned by the inspector at a desirable position.

Next, a method for carrying out an ingredient analysis of solder included in the waste printed-circuit board 1 using the first ingredient analysis apparatus 200 in accordance with the first embodiment configured as described above will be described. The waste printed-circuit board 1 serving as an object to be inspected is placed on a sample table 18. The sample table 18 is a belt conveyor, and is configures so as to transfer the printed-circuit board 1 serving as on object to be inspected one by one to an inspection position.

As shown in FIG. 2A, an electronic component 16 is mounted on the printed-circuit board 1, and the terminals of the electronic component 16 are connected with a land 15 of the printed-circuit board 1 via solder 17. With the solder 17 being a substance to be analyzed, the inspector locates the tip of the atmospheric pressure plasma source 2 in the close vicinity of the land 15 to which the solder 17 adheres. The tip of the light transmission part 6 is disposed in the close vicinity of the land 15. At the same time, an exhausting nozzle of the exhaust device 55 is disposed in the direction of the land 15. The printed-circuit board 1 is placed on the sample table 18 so that the solder 17 is face upward. An embodiment in which the sample table 18 is formed of resin is described; however, the sample table 18 may be configured with conductive materials. In this case, the sample table 18 must be grounded.

As shown in FIG. 2A, in the atmospheric pressure plasma source 2, the part that is in the closest vicinity of the solder 17 and contacts plasma 5 comprises the dielectric substance 12. The dielectric substance 12 is disposed at the tip of the discharge electrode 13 of the plasma size, and is configured so that the discharge electrode 13 to which high-frequency power is supplied does not directly face the substance to be analyzed. Inert gas from the gas supplying device 13, for example, helium gas flows through the gas passage 73 of the stainless pipe 71, the porous ceramic 72 having permeability to air and the gas passage 14 in the discharge electrode 13 as shown with an arrow.

After the atmospheric pressure plasma source 2, the light transmission part 6, and the exhaust nozzle of the exhaust device 55 are disposed as described above, a high-frequency power of 200 W (preferably, 10 W or more and 500 W or less) having a frequency of 13.56 MHz is supplied from a power source 4 while an inert gas, for example, helium gas) of 1000 sccm (preferably, approximately 100 sccm or more and 10 slm or less) is supplied from the gas supplying device 3 to the atmospheric pressure plasma source 2. As a result, the plasma 5 is generated between the atmospheric pressure plasma source 2 and the land 15. Via an optical fiber 6A of the light transmission part 6, the light from the substance to be analyzed to which the plasma 5 is applied is guided to a filter 7 capable of allowing light having a wavelength of 666 nm to pass through. The light having passed through the filter 7 is guided to the photodiode 8 and monitored. The plasma-side tip of the optical fiber 6A of the light transmission part 6 is an emission input section 100 which a light emitted from the substance to be analyzed, to which the plasma 5 is applied, enters.

The signal passed through the optical fiber 6A and obtained by photoelectrical conversion using the photodiode 8 is sent to the controller 9 of the ingredient analyzing part 200B. The controller 9 judges the presence or absence of a specific element in the solder 17 serving as a substance to be analyzed, using the emission of the plasma 5. A heavy metal element is excited and emits light when heated to high temperatures. The wavelength thereof is characteristic of the element, and the intensity increases in proportion to the content thereof. Therefore, through spectroscopic analysis of the light from the plasma 5 generated when the solder 17 is excited, it is possible to judge whether the substance to be analyzed is a lead-containing solder or a lead-free solder. In other words, if the intensity of the emission of the plasma 5 at a specific wavelength is higher than a predetermined value, it is judged that the solder 17 serving as a substance to be analyzed contains lead.

At the same time, when it is judged that lead is present, detection sound is generated from the speaker 10 and the indicator 11 is lit, thereby informing the inspector to that effect. In other words, in the ingredient analysis apparatus shown in FIG. 1, the ingredient analyzing part 200B is provided with an information section so that when a specific element, for example, lead is detected, the information section informs the inspector to that effect using sound or light.

The first ingredient analysis apparatus 200 as shown in FIG. 1 can be used when the emission peak of an element to be judged as to whether it is present or not in the substance to be analyzed is known beforehand. In the first ingredient analysis apparatus 200, light of a specific wavelength is taken out via the filter 7 and then the emission intensity of the light is measured. Accordingly, the first ingredient analysis apparatus 200 is an apparatus which can be configured at extremely low cost, and is easy in handling and compact in size.

Figure 3:
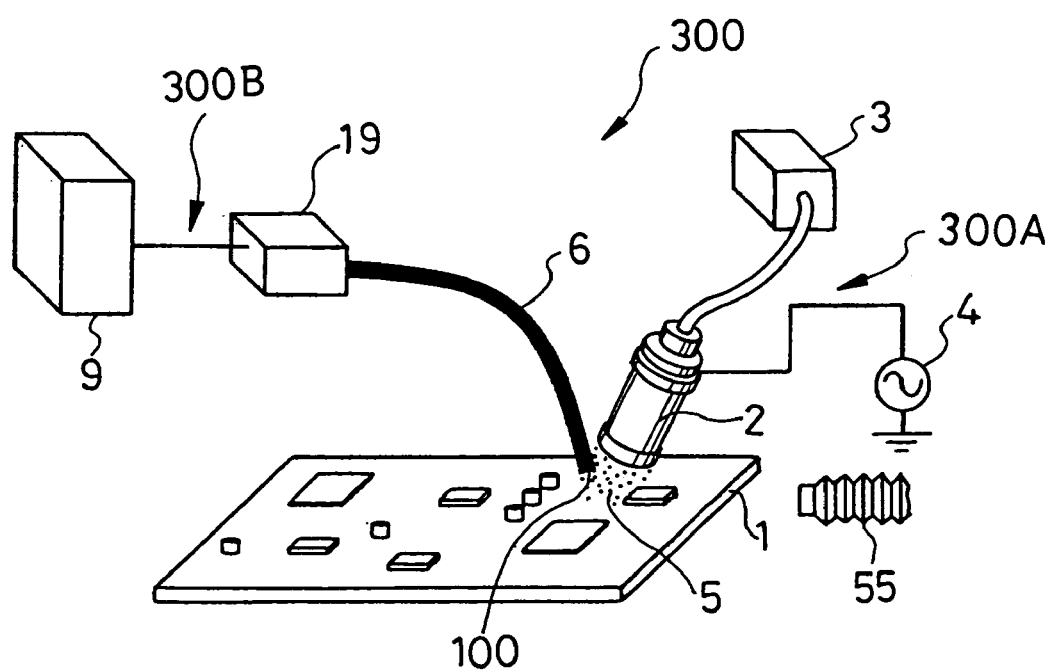
FIG. 3 is a view showing a second ingredient analysis apparatus in accordance with the first embodiment of the present invention.

In order to know beforehand the emission peak of the element to be judged as to whether it is present or not in the substance to be analyzed, a second ingredient analysis apparatus 300 shown in FIG. 3 is used. The second ingredient analysis apparatus 300 shown in FIG. 3 differs from the above-mentioned first ingredient analysis apparatus 200 in the configuration of an ingredient analyzing part 300B. A plasma generating part 300A of the second ingredient analysis apparatus 300 has the same configuration as the plasma generating part 200A of the first ingredient analysis apparatus 200. Accordingly, in the second ingredient analysis apparatus 300, components having the same function as those of the first ingredient analysis apparatus 200 are denoted by the same reference numerals and the description thereof are omitted.

In the second ingredient analysis apparatus 300 shown in FIG. 3, light from the optical fiber of the light transmission part 6 is supplied to a spectroscopic instrument 19, thereby to measure the emission intensity in a wider wavelength range than that of the first ingredient analysis apparatus 200. The second ingredient analysis apparatus 300 can also be used for analyzing substances whose ingredients are completely unknown.

Figure 4:
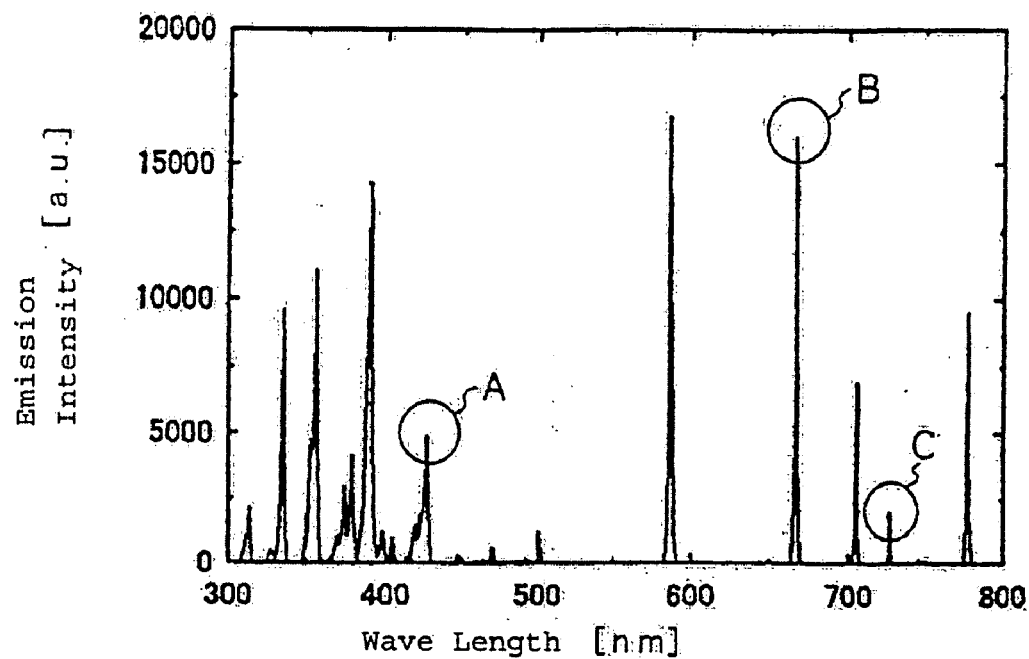
FIG. 4 is an emission spectrum obtained when a printed-circuit board on which electronic components are mounted using lead-containing solder is analyzed.
Figure 5:
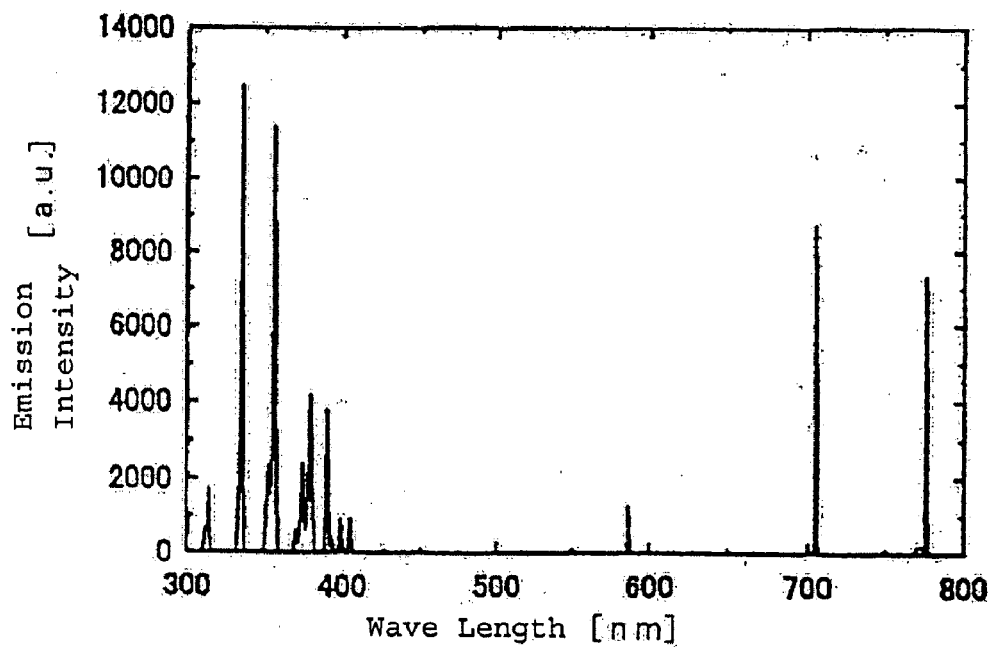
FIG. 5 is an emission spectrum obtained when a printed-circuit board on which electronic components are mounted using lead-free solder is analyzed.

FIG. 4 shows an emission spectrum obtained when a printed-circuit board on which electronic components are mounted using lead-containing solder is analyzed with the second ingredient analysis apparatus 300. In addition, FIG. 5 shows an emission spectrum obtained when a printed-circuit board on which electronic components are mounted using lead-free solder (primarily consisting of tin, silver and copper) is analyzed with the second ingredient analysis apparatus 300. When FIGS. 4 and 5 are compared, it is found that there are some emission peaks generated only in the case of lead-containing solder. In other words, these are peaks generated at wavelengths of 427 nm (a peak encircled by "A" in FIG. 4), 666 nm (a peak encircled by "B" in FIG. 4) and 730 nm (a peak encircled "C" in FIG. 4). It is conceivable that the peaks at these wavelengths are all caused by the emission peculiar to lead. Hence, by monitoring the level at one of these wavelengths, it is possible to make a judgment as to whether the solder used on the printed-circuit board serving as an object to be inspected is lead-containing solder or lead-free solder. For making the judgment more easily, the transmittable wavelength of the filter 7 should only be set at 427 nm, 666 nm or 730 nm using the apparatus configured as shown in FIG. 1.

The emission peaks of silver and copper do not appear in FIG. 5. It is conceivable that the amounts of silver and copper were scarce in the plasma because the boiling points of silver and copper are higher than that of lead. The boiling point of lead is 1750° C., the boiling point of silver is 2184° C., and the boiling point of copper is 2580° C.

As a criterion as to whether or not a substance to be analyzed contains a specific element, the value of a predetermined emission intensity at a specific wavelength is used. For example, it is judged whether the specific element is contained or not by as to whether a measured emission intensity is higher than a predetermined threshold value or not. Alternatively, it is judged whether the specific element is contained or not by measuring the emission intensities at two or more wavelengths and comparing as to whether or not the ratio of emission intensities thereof is higher than a predetermined threshold value. In this case, the emission peak of an inert gas supplied from the gas supplying device 3, for example, the emission peak (at 706 nm or the like) of helium, can be used as an emission peak to be a reference peak of the ratio of emission intensities. In this case, the emission intensities at two wavelengths are measured using two optical fibers, two filters and two photodiodes. Alternatively, it may also be possible that the light guided into one optical fiber is divided so as to pass through two paths by an optical divider and that monitoring is carried out in each path using a filter and a photodiode. In the case that the ratio of emission intensities is calculated as described above, it may be configured so that the magnitude of the ratio can be displayed by an indicator.

In the case that the emission peak of an inert gas is used as a reference peak, since the emission intensity thereof is not zero, it is possible to make a judgment as to whether discharge has occurred normally or not by calculating the ratio of emission intensities. This is advantageous in raising the reliability of the ingredient analysis.

Second Embodiment

An ingredient analysis apparatus in accordance with a second embodiment of the present invention will be described below referring to FIG. 6.

Figure 6:
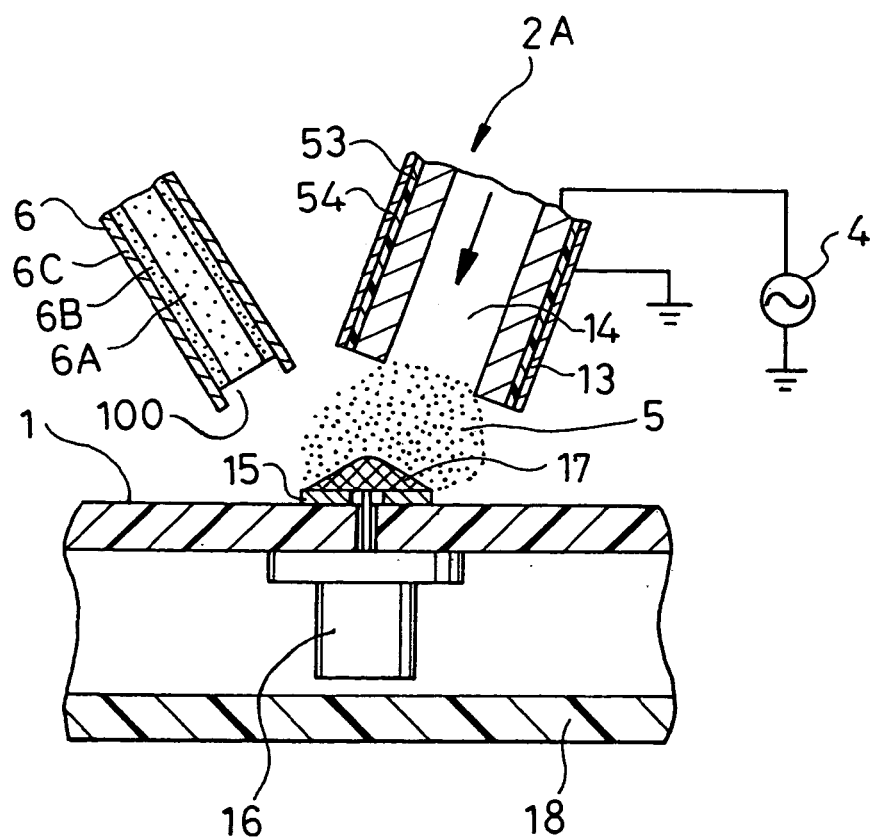
FIG. 6 is an enlarged cross-sectional view showing a portion for generating plasma in an ingredient analysis apparatus in accordance with a second embodiment of the present invention.

FIG. 6 is an enlarged cross-sectional view showing a portion for generating plasma in the ingredient analysis apparatus in accordance with the second embodiment of the present invention. In the second embodiment, components having the same function and configuration as those of the first embodiment are denoted by the same reference numerals and the description thereof are omitted. The ingredient analysis apparatus in accordance with the second embodiment differs from the ingredient analysis apparatuss in accordance with the first embodiment in the configuration of an atmospheric pressure plasma source 2A. As shown in FIG. 6, the atmospheric pressure plasma source 2A is provided with a discharge electrode 13 to which high-frequency power is supplied in the portion nearest to a substance to be analyzed (solder 17), more specifically in the portion making contact with plasma 5. In other words, in the second embodiment, a dielectric substance is not formed at the tip of the discharge electrode 13.

In the ingredient analysis apparatus in accordance with the second embodiment, an inert gas flows through a gas passage 14 inside the discharge electrode 13 in the direction indicated by the arrow, and then directly blow the solder 17 from the opening thereof. A terminal of an electronic component 16 mounted on a printed-circuit board 1 serving as an object to be inspected is joined to a land 15 formed on the printed-circuit board 1 using the solder 17. In addition, the printed-circuit board 1 is placed on a sample table 18.

In the ingredient analysis apparatus in accordance with the second embodiment configured as described above, the generated plasma 5 has a characteristic of being apt to become arc discharge. It is difficult to control arc discharge because of its instability. However, since part of the solder 17 being used for joint jumps out relatively abundantly in the plasma 5, the use of the arc discharge is advantageous in raising analysis sensitivity. However, in order that the atmospheric pressure plasma source 2 and a power source 4 are prevented from being damaged by a large discharge current, it is desirable that continuous discharge time should be one second or less. In the ingredient analysis, the analysis can be done sufficiently in this short time.

In the ingredient analysis apparatus in accordance with the second embodiment, the discharge electrode 13 of the atmospheric pressure plasma source 2A is connected to the power source 4, to which high-frequency power is supplied. On the other hand, the cover 54 as a sheath of the atmospheric pressure plasma source 2 is grounded. Therefore, the atmospheric pressure plasma source 2A has a configuration that an inspector can move the atmospheric pressure plasma source 2A manually with respect to the printed-circuit board 1 as an object to be inspected, and thereby locating it at a desirous position with respect to the printed-circuit board 1.

Third Embodiment

An ingredient analysis apparatus in accordance with a third embodiment of the present invention will be described below referring to FIG. 7.

Figure 7:
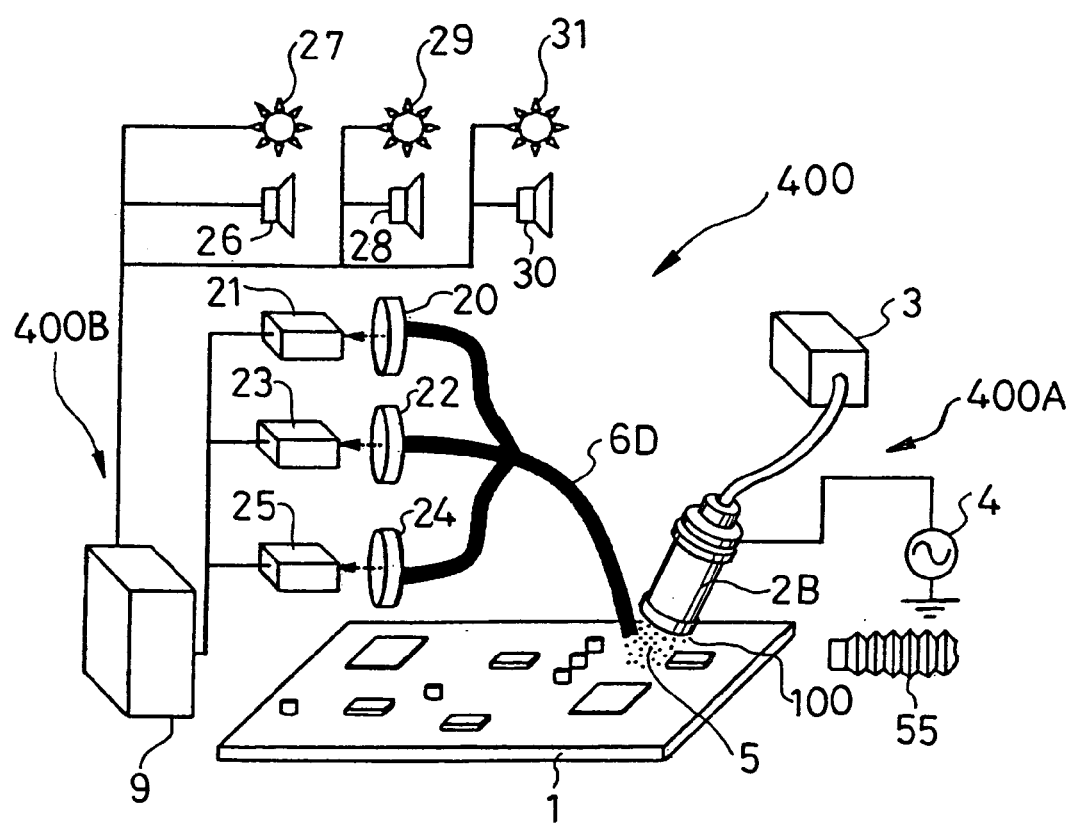
FIG. 7 is a view showing a schematic configuration of an ingredient analysis apparatus in accordance with a third embodiment of the present invention.

FIG. 7 is a schematic view showing the ingredient analysis apparatus in accordance with the third embodiment of the present invention. In the third embodiment, components having the same function and configuration as those of the first embodiment are denoted by the same reference numerals and the description thereof are omitted. An ingredient analysis apparatus 400 in accordance with the third embodiment differs from the first ingredient analysis apparatus 200 in accordance with the first embodiment in the configuration of an ingredient analyzing part 400B. An atmospheric pressure plasma source 400A has the same configuration as the atmospheric pressure plasma source 200A of the first embodiment.

As shown in FIG. 7, in the ingredient analysis apparatus 400 of the third embodiment, the exit of a light transmission part 6D is divided into three exits. The exits are provided with filters 20, 22, 24, respectively, according to each optical axis, and light having passed through the filters 20, 22, 24 is guided via photodiodes 21, 23, 25, respectively, to be monitored. The signal obtained by photoelectrical conversion using the photodiodes 21, 23, 25 is transmitted to a controller 9 of the ingredient analyzing part 400B. In the ingredient analysis apparatus 400 of the third embodiment, the three filters 20, 22, 24 pass light each having different wavelength. The controller 9 judges the presence or absence of three elements in the substance to be analyzed, using the emission intensities with respect to the three wavelengths of the emission of plasma 5. When it is judged that the respective elements are present in the substance to be analyzed, detection sound is generated from corresponding speakers 26, 28, 30 and corresponding indicators 27, 29 and 31 are lit.

The specific operation of the ingredient analysis apparatus 400 of the third embodiment configured as described above will be hereinafter described.

As shown in FIG. 7, using a solder on a printed-circuit board 1 as a substance to be an analyzed, a pressure plasma source 2B is disposed near a land to which the solder is attached. A high-frequency power of 200 W having a frequency of 13.56 MHz is supplied from a power source 4 while an inert gas (such as helium gas) of 1000 sccm is supplied from a gas supplying device 3 to the atmospheric pressure plasma source 2B. As a result, plasma 5 is generated between the atmospheric pressure plasma source 2B and the land. The emission of the generated plasma 5 is guided into an optical fiber of the light transmission part 6D and divided so as to pass through three paths in the middle of the fiber. The light guided to the first filter 20 passes through the first filter 20, is further guided to the first photodiode 21, and monitored.

The light guided to the second filter 22 passes through the second filter 22, is further guided to the second photodiode 23, and monitored. The light guided to the third filter 24 passes through the third filter 24, is further guided to the third photodiode 25, and monitored. The plasma-side tip of the optical fiber is an emission input section 100. The signals obtained by photoelectrical conversion using the photodiodes 21, 23 and 25 are sent to the controller 9 of the ingredient analyzing part 400B. The controller 9 judges the presence or absence of elements in the substance to be analyzed, using the light of the plasma 5. Since the three filters 20, 22, 24 having different transmittable wavelengths are used, the presence or absence of three elements can be judged. If it is judged that a specific element is present, detection sound is generated from the first speaker 26 and the first indicator 27 is lit, thereby informing the inspector that the element is present. If another element is detected, detection sound is generated from the second speaker 28 and the second indicator 29 is lit, thereby informing the inspector that the element is present. Furthermore, if still another element is detected, detection sound is generated from the third speaker 30 and the third indicator 31 is lit, thereby informing the inspector that the element is present.

Furthermore, it is possible to detect whether a specific element, for example, lead is present or not in the substance to be analyzed using the ingredient analysis apparatus 400 of the third embodiment. In other words, if the emission intensities of the plasma 5 at specific three wavelengths are respectively higher than a predetermined value at each wavelength, it is judged that the specific element is present in the substance to be analyzed. For example, assuming that the substance to be analyzed is solder and the element to be judged is lead, the three wavelengths are of 427 nm ("A" in FIG. 4), 666 nm ("B" in FIG. 4) and 730 nm ("C" in FIG. 4). By judging the substance to be analyzed using emission intensities at three wavelengths, it is possible to make highly accurate judgment.

Fourth Embodiment

An ingredient analysis apparatus in accordance with a fourth embodiment of the present invention will be described below referring to FIG. 8.

Figure 8:
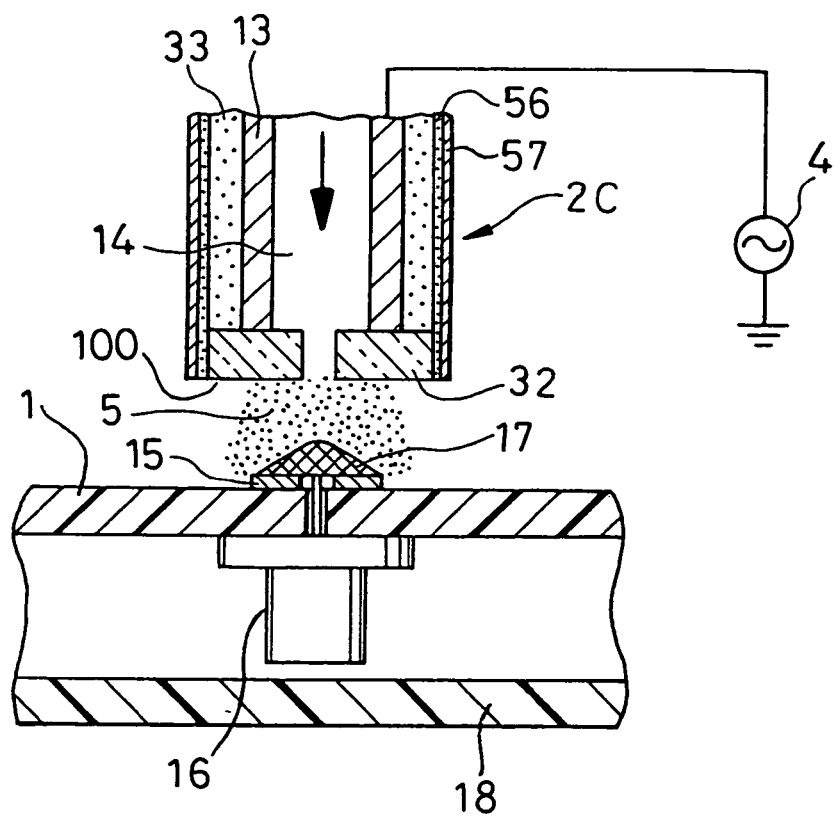
FIG. 8 is an enlarged cross-sectional view of a portion for generating plasma in an ingredient analysis apparatus in accordance with a fourth embodiment of the present invention.

FIG. 8 is an enlarged cross-sectional view showing a portion for generating plasma in the ingredient analysis apparatus in accordance with the fourth embodiment of the present invention. In the forth embodiment, components having the same function and configuration as those of the first embodiment are denoted by the same reference numerals and the description thereof are omitted. The ingredient analysis apparatus in accordance with the forth embodiment differs from the first ingredient analysis apparatus 200 in accordance with the first embodiment in the configuration of an atmospheric pressure plasma source 2C in a plasma generating section. In the ingredient analysis apparatus in accordance with the forth embodiment, the atmospheric pressure plasma source 2C is provided with a light transmission part.

In FIG. 8, in the atmospheric pressure plasma source 2C, a tip portion 32 disposed nearest to a substance to be analyzed and making contact with plasma 5 is formed of a transparent material, such as quartz glass. This tip portion 32 is secured to the plasma-side tip of a discharge electrode 13, and power is supplied to this discharge electrode 13. Inert gas, such as helium gas, flows through the gas passage 14 inside the discharge electrode 13 in the direction indicated by the arrow. A terminal of an electronic component 16 positioned and mounted on a land 15 provided on a printed-circuit board 1 is joined to the land 15 using solder 17. In addition, the printed-circuit board 1 is placed on a sample table 18. A transparent tube 33 is provided around the discharge electrode 13. The tip portion 32 has a function of an emission input section 100, and the transparent tube 33 has a function of an optical path. The light incident from the plasma 5 is guided into an optical fiber (not shown) connected to the transparent tube 33. And the light guided into the optical fiber reaches a photodiode via a filter and then is photoelectrically converted. The photoelectrically converted signal is input to a controller, and then the emission intensity at a specific wavelength is measured therein. Alternatively, it is possible to configure so that the light guided into the optical fiber enters a spectroscopic instrument and then the emission intensity at a wide range of wavelength can be monitored therein.

In the ingredient analysis apparatus in accordance with the forth embodiment configured as described above, it is not necessary to obliquely set the atmospheric pressure plasma source 2C with respect to the substance to be analyzed, and the emission input section 100 can securely be disposed near the plasma 5. This can improve the reliability of the analysis results of the ingredient analysis apparatus in accordance with the fourth embodiment.

Fifth Embodiment

Figure 9:
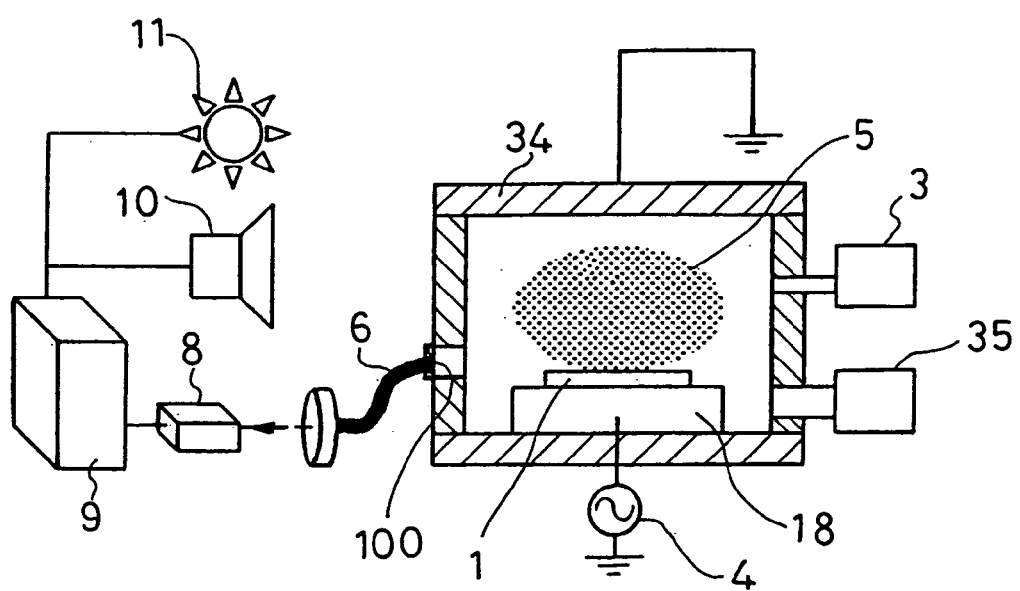
FIG. 9 is a view showing a schematic configuration of an ingredient analysis apparatus in accordance with a fifth embodiment of the present invention.

An ingredient analysis apparatus in accordance with a fifth embodiment of the present invention will be described below referring to FIG. 9. FIG. 9 is a schematic view showing the ingredient analysis apparatus in accordance with the fifth embodiment of the present invention.

In the fifth embodiment, components having the same function and configuration as those of the first embodiment are denoted by the same reference numerals and the description thereof are omitted. The ingredient analysis apparatus in accordance with the fifth embodiment differs from the first ingredient analysis apparatus 200 in accordance with the first embodiment in the configuration of an atmospheric pressure plasma source in a plasma generating part. In the ingredient analysis apparatus in accordance with the fifth embodiment, the atmospheric pressure plasma source is disposed in a body.

In FIG. 9, a printed-circuit board 1 serving as a substance to be analyzed is placed inside a vacuum vessel 34. A high-frequency power of 300 W having a frequency of 13.56 MHz is supplied from a power source 4 to a sample electrode of the sample table 18 while helium gas serving as an inert gas is supplied into the vacuum vessel 34 and exhausted from the vacuum vessel 34 using a pump 35 serving as an exhaust device. Plasma 5 is thus generated inside the vacuum vessel 34. The emission of the plasma 5 is guided into an optical fiber of a light transmission part 6. Via the optical fiber, the light is guided to a filter 7 capable of allowing light having a wavelength of 666 nm to pass through. The light having passed through the filter 7 is guided by a photodiode 8 and monitored. The plasma-side tip of the optical fiber is disposed in a hole formed in the wall of the vacuum vessel 34. The tip of the optical fiber provided in the hole in the wall of the vacuum vessel 34 is an emission input section 100.

The signal obtained by photoelectrical conversion using the photodiode 8 is sent to a controller 9 serving as an emission analysis section. The controller 9 judges the presence or absence of an element in the substance to be analyzed, using the light of the plasma 5. In other words, if the intensity of the emission is higher than a predetermined value, it is judged that a specific element, for example, lead is present in the substance to be analyzed. If it is judged that a specific element is present, detection sound is generated from a speaker 10 and an indicator 11 is lit, thereby informing the inspector of that effect. In other words, the ingredient analysis apparatus in accordance with the fifth embodiment is provided with an information section so that when a specific element is detected, the information section informs the operator of that effect using sound or light.

The ingredient analysis apparatus in accordance with the fifth embodiment has an excellent advantage of being capable of stably applying the plasma 5 to a substance to be analyzed, having a given shape, although some advantages (no air-tight vessel or pump is required, very low-priced localized analysis is made easy, analysis in a short time is made possible, and the like) are lost, which are advantages obtained by using atmospheric pressure plasma. In other words, in the ingredient analysis apparatus in accordance with the fifth embodiment, it is not necessary to set the positions of the atmospheric pressure plasma source and the emission input section 100 with respect to the substance to be analyzed. Hence, the plasma 5 can be applied stably and easily to the substance to be analyzed, and reliable ingredient analysis can be carried out.

Sixth Embodiment

An ingredient analysis apparatus and an ingredient analysis method in accordance with a sixth embodiment of the present invention will be described below referring to FIG. 10. The ingredient analysis apparatus in accordance with the sixth embodiment has the same configuration as the ingredient analysis apparatus in accordance with the first embodiment. The sixth embodiment differs from the first embodiment in an ingredient analysis method using the ingredient analysis apparatus. Accordingly, components having the same function and configuration as those of the first embodiment are denoted by the same reference numerals and the description thereof are omitted.

Figure 10:
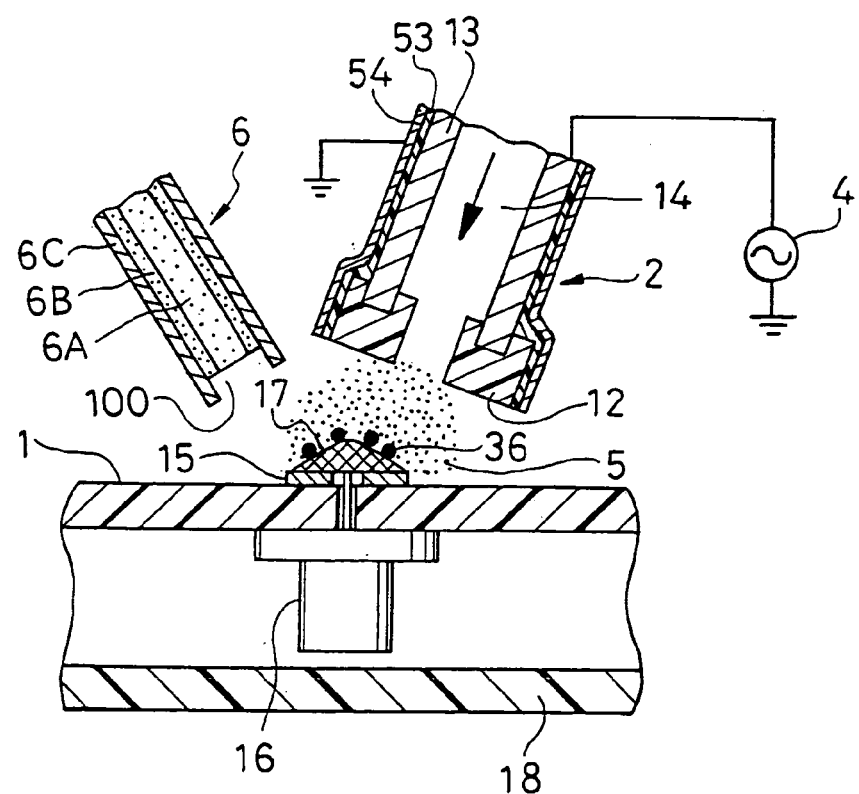
FIG. 10 is an enlarged cross-sectional view of a portion for generating plasma in an ingredient analysis apparatus in accordance with a sixth embodiment of the present invention.

In FIG. 10, in an atmospheric pressure plasma source 2, the portion disposed nearest to the substance to be analyzed and making contact with plasma 5 is provided with a dielectric substance 12. This dielectric substance 12 is provided at the plasma-side tip of a discharge electrode 13, and the power is supplied to this discharge electrode 13. An inert gas, such as helium gas, flows through the gas passage 14 inside the discharge electrode 13 in the direction indicated by the arrow. A printed-circuit board 1 serving as an object to be inspected is placed and transferred on a sample table 18. A terminal of an electronic component 16 positioned and mounted on a land 15 provided on the printed-circuit board 1 is joined to the land 15 using solder 17.

In the ingredient analysis method of the sixth embodiment, first, the solder 17 serving as a substance to be analyzed is ground to form a ground debris 36 on the surface of the solder 17 (grinding step). Next, as described in the above-mentioned first embodiment, the solder 17 as a substance to be analyzed is excited to allow the plasma 5 to emit light. In the ingredient analysis method of the sixth embodiment, since the ground debris 36 is attached on the surface of the solder 17, the ground debris 36 on the surface of the solder 17 is excited and allows the plasma to emit light as shown in FIG. 10.

As mentioned above, in the ingredient analysis method using the ingredient analysis apparatus in accordance with the sixth embodiment, the surface area of the substance to be analyzed, making contact with the plasma 5, increases, whereby detection sensitivity is improved. In the ingredient analysis method of the sixth embodiment, an embodiment using the ingredient analysis apparatus in accordance with the first embodiment is described; however, it is possible to use the ingredient analysis apparatuss of the above-mentioned second embodiment from the forth embodiment and of the below-mentioned eight embodiment from the eleventh embodiment.

Seventh Embodiment

An ingredient analysis apparatus and an ingredient analysis method in accordance with a seventh embodiment of the present invention will be described below referring to FIG. 11. The ingredient analysis apparatus in accordance with the seventh embodiment has a same configuration as the ingredient analysis apparatuss in accordance with the first embodiment. The seventh embodiment differs from the first embodiment in an ingredient analysis method using an ingredient analysis apparatus. Accordingly, components having the same function and configuration as those of the first embodiment are denoted by the same reference numerals and the description thereof are omitted.

Figure 11:
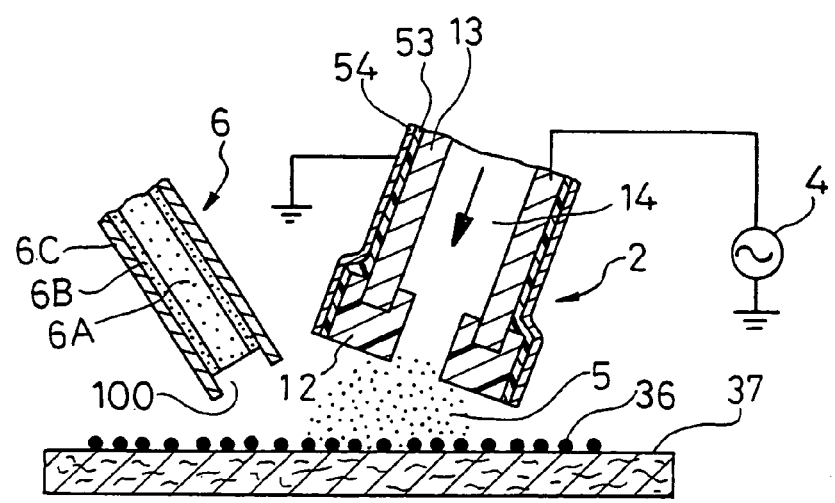
FIG. 11 is an enlarged cross-sectional view of a portion for generating plasma in an ingredient analysis apparatus in accordance with a seventh embodiment of the present invention.

In FIG. 11, in an atmospheric pressure plasma source 2, the portion disposed nearest to the substance to be analyzed, that is a portion making contact with plasma 5, is provided with a dielectric substance 12. This dielectric substance 12 is provided at the plasma-side tip of a discharge electrode 13, and high-frequency power is supplied to this discharge electrode 13. An inert gas, such as helium gas, flows through a gas passage 14 inside the discharge electrode 13 in the direction indicated by the arrow.

In the seventh embodiment, a printed-circuit board 1 serving as an object to be inspected is not directly inspected. Instead, solder serving as a substance to be analyzed on the printed-circuit board 1 is ground and a ground debris thereof is used as an object to be inspected.

In the ingredient analysis method of the seventh embodiment, first, solder serving as a substance to be analyzed is ground (grinding step). A ground debris is formed on the surface of a grinding pad 37 used in the grinding step. The grinding pad 37 used in this embodiment is a cloth file; however, a lead-free grindstone may be used.

Next, as shown in FIG. 11, plasma 5 is generated with respect to a ground debris 36 formed on the surface of the grinding pad 37, using the atmospheric pressure plasma source 2. In order to generate the plasma 5, the dielectric substance 12 is provided at the plasma-side tip of the discharge electrode 13, and the power is supplied to the discharge electrode 13. An inert gas, such as helium gas, flows through the gas passage 14 inside the discharge electrode 13 in the direction indicated by the arrow. The light resulted from generation of the plasma 5 is analyzed by spectroscopic analysis, whereby the substance to be analyzed is inspected.

With this analysis method, the surface area of the substance (ground debris) made of the same material as that of the substance to be analyzed, making contact with the plasma 5, increases, whereby detection sensitivity is improved.

Eighth Embodiment

An ingredient analysis apparatus in accordance with an eighth embodiment of the present invention will be described below referring to FIG. 12.

Figure 12:
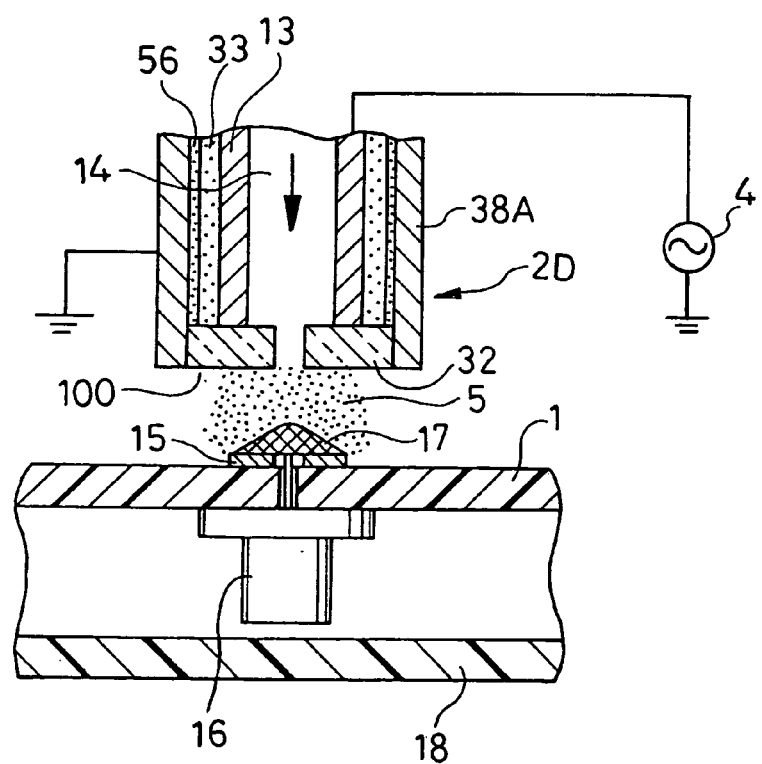
FIG. 12 is an enlarged cross-sectional view of a portion for generating plasma in an ingredient analysis apparatus in accordance with an eighth embodiment of the present invention.

FIG. 12 is an enlarged cross-sectional view showing a portion for generating plasma in the ingredient analysis apparatus in accordance with the eighth embodiment of the present invention.

In the eighth embodiment, components having the same function and configuration as those of the first embodiment are denoted by the same reference numerals and the description thereof are omitted. The ingredient analysis apparatus in accordance with the eighth embodiment differs from the first ingredient analysis apparatus 200 in accordance with the first embodiment in the configuration of an atmospheric pressure plasma source 2D of a plasma generating part.

In FIG. 12, in an atmospheric pressure plasma source 2D of the ingredient analysis apparatus in accordance with the eighth embodiment, a tip portion 32 disposed nearest to a substance to be analyzed and making contact with plasma 5 is formed of a transparent material, such as quartz glass. Since the contents of impurities of quarts glass are small, the emission spectrum is not thus disturbed, making it possible to make a highly accurate inspection. Moreover, since the quarts glass is resistant to etching by the plasma 5, it is durable for a long time. This tip portion 32 formed of quarts glass is provided at the plasma-side tip of a discharge electrode 13, and the power is supplied to the discharge electrode 13. An inert gas, such as helium gas, flows through a gas passage 14 inside the discharge electrode 13 in the direction indicated by the arrow. A terminal of an electronic component 16 positioned and mounted on a land 15 provided on a printed-circuit board 1 is joined to the land 15 using solder 17. In addition, the printed-circuit board 1 is placed on a sample table 18. A transparent tube 33 made of resin that allows transparent light to pass through is provided around the discharge electrode 13. The tip portion 32 and the transparent tube 33 have a function of an emission input section 100. The light incident to the transparent tube 33 via the tip portion 32 is guided to an optical fiber (not shown) and sent to an emission monitoring device, that is to the ingredient analyzing part 200B comprising the filter 7, the photodiode 8 and the controller 9, etc. shown in FIG. 1, or to the ingredient analyzing part 300B comprising the spectroscopic instrument as shown in FIG. 3. Furthermore, a coating layer 56 is formed on the external circumference face of the transparent tube 33. The coating layer 56 is formed using resin having translucency and made of different materials so that the light incident on the transparent tube 33 will not leak. A grounded conductive pipe 38A is further provided around the external circumference face thereof.

With the ingredient analysis apparatus in accordance with the eighth embodiment configured as described above, the discharge electrode 13 is enclosed with the tip portion 32, the transparent tube 33 and the grounded conductive pipe 38A, whereby the leakage of high-frequency noise is suppressed, and the safety of the inspector is improved.

Ninth Embodiment

An ingredient analysis apparatus in accordance with a ninth embodiment of the present invention will be described below referring to FIG. 13.

Figure 13:
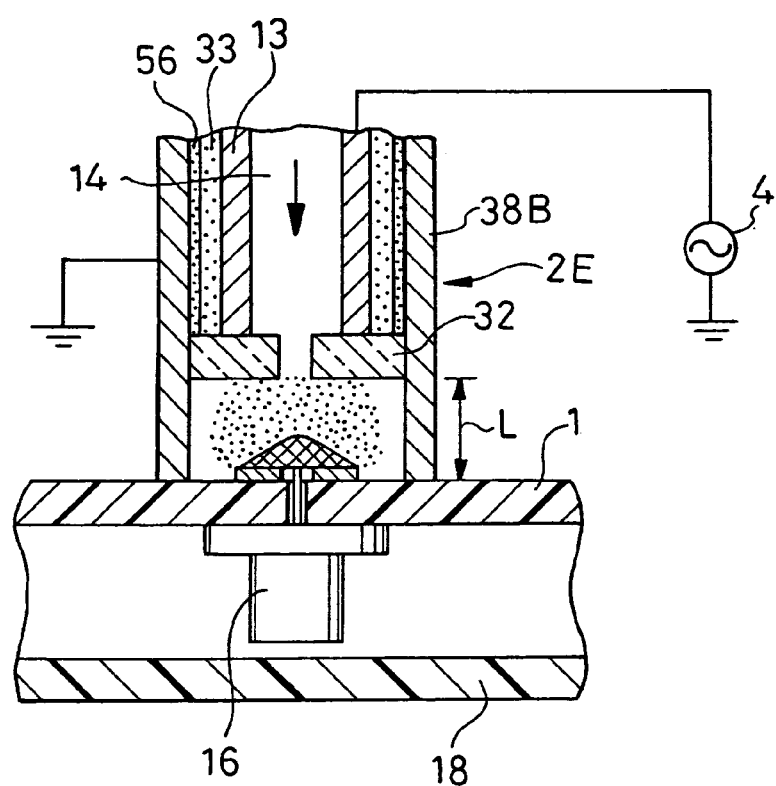
FIG. 13 is an enlarged cross-sectional view of a portion for generating plasma in an ingredient analysis apparatus in accordance with a ninth embodiment of the present invention.

FIG. 13 is an enlarged cross-sectional view showing a section for generating plasma as an atmospheric pressure plasma source in the ingredient analysis apparatus in accordance with the ninth embodiment of the present invention. In the ninth embodiment, components having the same function and configuration as those of the first embodiment are denoted by the same reference numerals and the description thereof are omitted. An atmospheric pressure plasma source 2E of the ingredient analysis apparatus in accordance with the ninth embodiment, as shown in FIG. 13, has a shape that the tip of the conductive tube 38A of the ingredient analysis apparatus in accordance with the eighth embodiment of the present invention as shown in FIG. 12 is extended. In other words, a conductive tube 38B in the ingredient analysis apparatus in accordance with the ninth embodiment is extended in the direction of plasma generation and is configured so as to make contact with the face of a printed-circuit board as an object to be inspected.

Since the tip of the conductive tube 38B of the atmospheric pressure plasma source 2E in the ingredient analysis apparatus in accordance with the ninth embodiment makes contact with the surface of the object to be inspected as described above, the gap between a printed-circuit board 1 serving as an object to be inspected and a discharge electrode 13 is kept constant at a certain distance (L). As a result, the gap between the substance to be analyzed and the discharge electrode is kept at a predetermined distance, thereby enabling plasma processing to be carried out with an appropriate discharge gap. In other words, the tip portion of the conductive tube 38B of the ingredient analysis apparatus in accordance with the ninth embodiment has a function of a spacer. Hence, the ingredient analysis apparatus in accordance with the ninth embodiment has an advantage of being capable of carrying out plasma processing stably.

Figure 14:
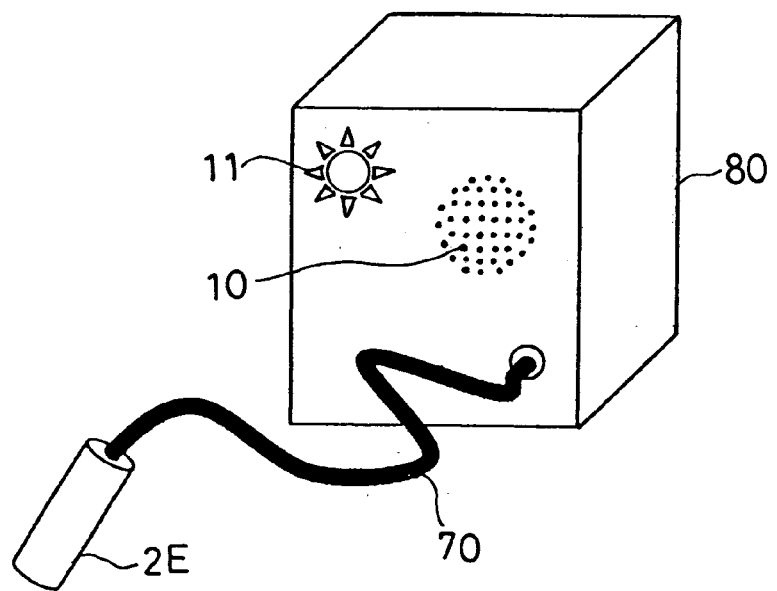
FIG. 14 is a view showing a configuration of the ingredient analysis apparatus in accordance with the ninth embodiment of the present invention.

FIG. 14 is an external view of the ingredient analysis apparatus in accordance with the ninth embodiment configured to be a hand-held type that is portable. The atmospheric pressure plasma source 2E of the hand-held type ingredient analysis apparatus as shown in FIG. 14 is a detection head, and is connected to a body 80 using a flexible cable 70. The flexible cable 70 is internally provided with a gas passage of an inert gas, a light path of an optical fiber, and an electrical wiring. The body 80 of this ingredient analysis apparatus is provided with a speaker 10 and an indicator 11 serving as an information section. The hand-held type ingredient analysis apparatus configured as such makes it possible to easily carry out an inspection of the substance to be analyzed regardless of time and place.

Figure 15:
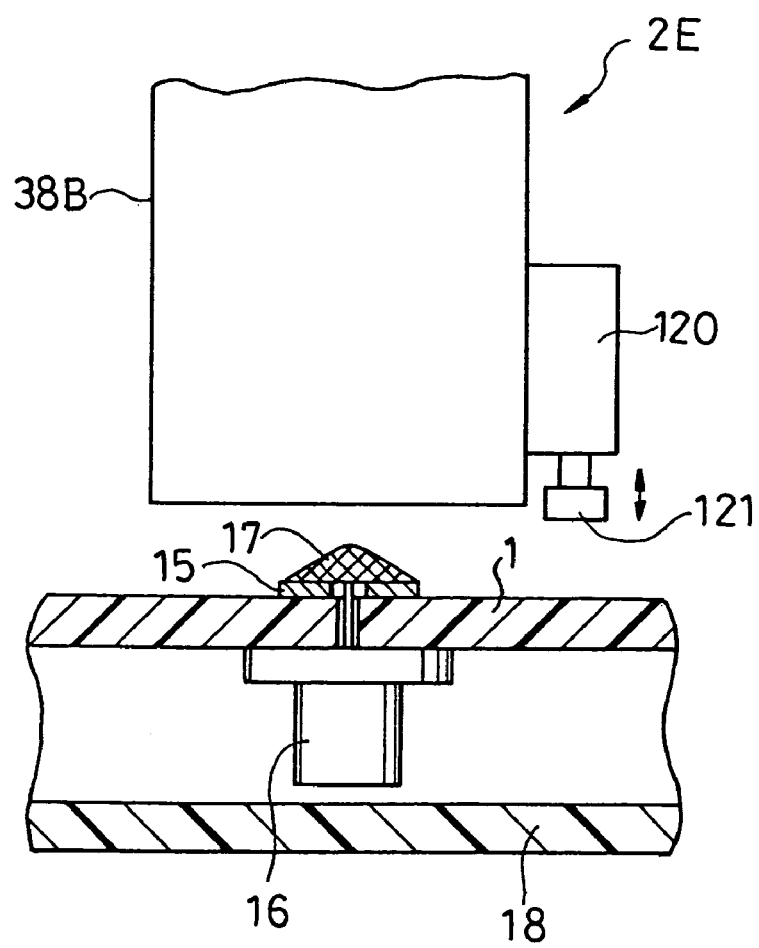
FIG. 15 is a view showing another configuration of an ingredient analysis apparatus in accordance with the ninth embodiment of the present invention.

FIG. 15 is a view showing an example in which a start switch 120 is additionally provided with atmospheric pressure plasma source 2E of the ingredient analysis apparatus in accordance with the ninth embodiment. As shown in FIG. 15, a protruded button 121 is provided below the start switch 120. The button 121 is pushed as a detection head when the atmospheric pressure plasma source 2E is made contact with the object to be inspected, whereby the ingredient analysis apparatus becomes ON-state. When the ingredient analysis apparatus becomes ON-state, an inert gas is discharged from the detection head, and at the same time high-frequency power is applied to the discharge electrode in the detection head. In the ingredient analysis apparatus configured as mentioned above, since the start switch 120 is disposed in the atmospheric pressure plasma source 2E, when the inspector operates the detection head by hand, ingredient analysis processing can be carried out surely and easily. Furthermore, the ingredient analysis apparatus in accordance with the ninth embodiment has an excellent effect wherein the application time of expensive inert gas can be shortened and the power consumption can be minimized.

Tenth Embodiment

An ingredient analysis apparatus in accordance with a tenth embodiment of the present invention will be described below referring to FIG. 16.

Figure 16:
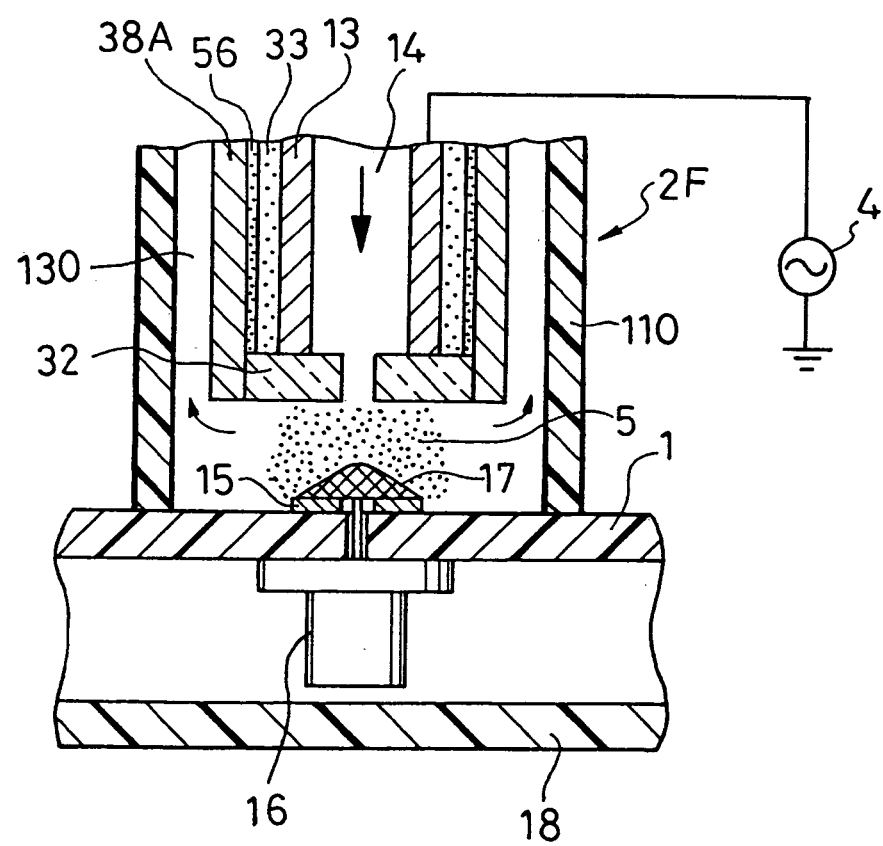
FIG. 16 is an enlarged cross-sectional view showing a portion for generating plasma in an ingredient analysis apparatus in accordance with a tenth embodiment of the present invention.

FIG. 16 is an enlarged cross-sectional view showing a portion for generating plasma in the ingredient analysis apparatus in accordance with the tenth embodiment of the present invention. The ingredient analysis apparatus in accordance with the tenth embodiment as shown in FIG. 16 is the analyzer that an exhaust mechanism is additionally provided with the above-mentioned atmospheric pressure plasma source 2D in accordance with the eighth embodiment of the present invention as shown in FIG. 12.

As shown in FIG. 16, in an atmospheric pressure plasma source 2F of the ingredient analysis apparatus in accordance with the tenth embodiment, an exhaust path 130 is formed on a conductive pipe 38A on the outside thereof. The periphery face of the the atmospheric pressure plasma source 2F is configured with an outer tube 110 made of resin. The outer tube 110 is extended from a tip portion 32 formed by quartz glass, and is configured so that the inspection is carried out by making the tip portion of the atmospheric pressure plasma source 2F contact with the object to be inspected.

As mentioned above, since the ingredient analysis apparatus in accordance with the tenth embodiment has a configuration in which the tip portion of the outer tube 110 of the atmospheric pressure plasma source 2F contacts with the surface of the object to be inspected, the gap between a printed-circuit board 1 and a discharge electrode 13 is kept at a constant distance. As a result, the ingredient analysis apparatus in accordance with the tenth embodiment can carry out the plasma processing with an appropriate discharge gap. In other words, the outer tube 110 of ingredient analysis apparatus in accordance with the tenth embodiment forms the exhaust path 130 and the tip portion thereof has a function of a spacer for keeping the discharge gap. The ingredient analysis apparatus in accordance with the tenth embodiment, therefore, has an excellent advantage that exhaust can be carried out without fail and stable plasma processing can be carried out.

Eleventh Embodiment

Figure 17:
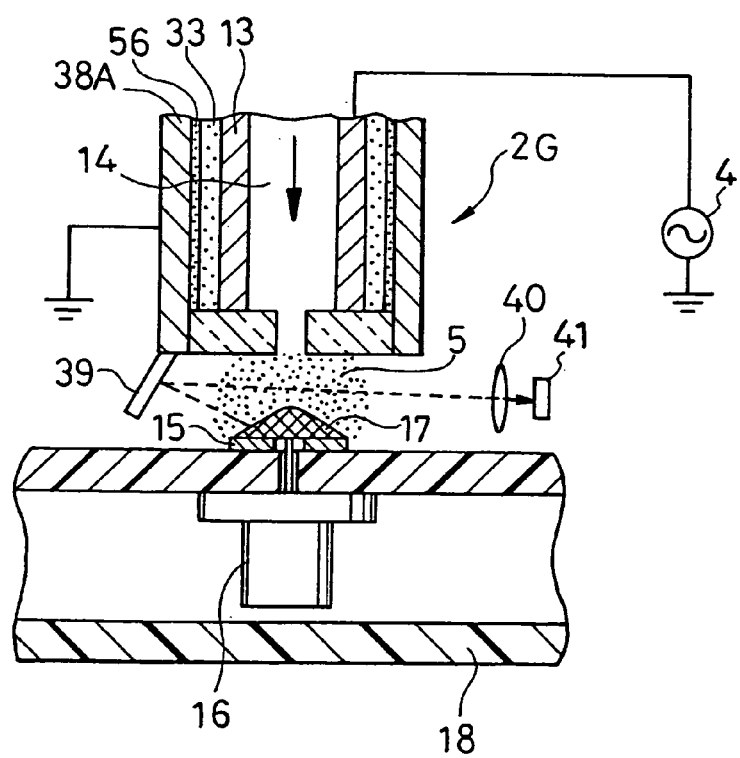
FIG. 17 is an enlarged cross-sectional view showing a portion for generating plasma in an ingredient analysis apparatus in accordance with an eleventh embodiment of the present invention.

An ingredient analysis apparatus in accordance with an eleventh embodiment of the present invention will be described below referring to FIG. 17. FIG. 17 is an enlarged cross-sectional view showing a portion for generating plasma in the ingredient analysis apparatus in accordance with the eleventh embodiment of the present invention.

As shown in FIG. 17, an atmospheric pressure plasma source 2G of the ingredient analysis apparatus in accordance with the eleventh embodiment has a configuration wherein a mirror 39 is additionally provided with the atmospheric pressure plasma source 2D of the ingredient analysis apparatus in accordance with the eighth embodiment of the present invention shown in FIG. 12. The pressure plasma source 2G is configured so that the light from the substance to be analyzed reflected by the mirror 39 passes through a lens 40, and an image is received by a CCD 41. The mirror 39, the lens 40 and the CCD 41 of the ingredient analysis apparatus in accordance with the eleventh embodiment constitute a monitor section. The ingredient analysis apparatus in accordance with the eleventh embodiment configured as described above can record an image together with measured values as a condition of the substance to be analyzed in the recording section (not shown) of a controller 9 using the above-mentioned monitor section. Furthermore, the light of plasma 5 can be directly monitored by visual inspection.

Since the ingredient analysis apparatus in accordance with the eleventh embodiment configured as described above can monitor emission at a measurement position, the state of the emission can be measured in real time, and an analysis result and an image corresponding thereto can be recorded as a set.

Furthermore, in the ingredient analysis apparatus in accordance with the eleventh embodiment, the atmospheric pressure plasma source 2G can be used as a hand-held type detection head having a diameter of approximately 10 to 50 mm as shown in FIG. 14. In this case, an optical fiber or electrical wiring extended from the detection head is configured with a flexible cable 70 as shown in FIG. 14.

Some configuration examples are described as plasma sources in the above-mentioned embodiments in accordance with the present invention. However, it is possible that other various plasma sources can also be used.

The case wherein helium gas serving as an inert gas is used as a discharge gas is taken as an example in the respective embodiments. However, it is also possible to use a mixture of other rare gasses, such as neon, argon and xenon. The use of rare gasses has advantages. For example, emission peaks are simple, atmospheric pressure plasma can be generated easily, and safety can be ensured.

The case wherein plasma is generated using high-frequency power having a frequency of 13.56 MHz is taken as an example in the respective embodiments. However, it is also possible to generate plasma using high-frequency power having a frequency of several hundred kHz to several GHz. Alternatively, DC power may also be used, or pulse power may also be supplied to the discharge electrode 13. The use of pulse power is advantageous in that no inert gas is necessary for the generation of atmospheric pressure plasma (discharge is possible even if air is used). In the case where DC power is used, it is preferable that a sample table 18 is configured with a conductor and is grounded.

The case wherein power is supplied to the discharge electrode is taken as an example in the respective embodiments. However, it is also possible to have a configuration wherein the sample table is configured as a sample electrode, and power is supplied to the sample electrode or a substance to be analyzed. Alternatively, it is possible to have a configuration wherein power is directly supplied to the substance to be analyzed.

The case wherein a wavelength of 427 nm, 666 nm or 730 nm is taken as an example of the emission wavelength suited for lead detection in the above-mentioned first embodiment. However, it is also possible to use other wavelengths, such as 220 nm being used for ICP emission analysis.

The case wherein a plurality of elements are analyzed using a branched optical fiber configuration is taken as an example in the above-mentioned third embodiment. However, it is also possible to have a configuration wherein, instead of light path branching, sequential switching of a plurality of filters having different transmittable wavelengths is carried out so that a plurality of elements can be analyzed.

In the above-mentioned respective embodiments, the case wherein atmospheric pressure plasma is used and the case wherein vacuum plasma is used (the fifth embodiment) are taken as examples. In the case that plasma generated at approximately atmospheric pressure is used, numerous advantages are obtained. For example, no air-tight vessel or pump is required, very low-priced localized analysis is made easy, and analysis in a short time is made possible.

In the present invention, it is also possible to have a configuration wherein a substance to be analyzed is ground, ground debris thus formed on the surface of the substance to be analyzed is placed inside a vacuum vessel, and plasma is generated inside the vacuum vessel. In this configuration, the emission of the plasma is monitored, and the presence or absence of an element in the substance is judged, using the emission of the plasma. In this case, the surface area of the substance making contact with the plasma is larger than that in the case wherein the substance is placed inside the vacuum vessel without being ground, whereby detection sensitivity is improved. In this case, it is possible to use an ingredient analysis apparatus comprising a grinding section having a grinding pad, a vacuum vessel, a sample electrode for allowing a sample to be placed inside the vacuum vessel, a power source for supplying power to the sample electrode, an emission input section and an emission analysis section.

In the respective embodiments, the case wherein lead is detected is taken as an example. However, the element to be detected may be silver, bismuth or indium. In this case, it is possible to separately recover printed-circuit boards and the like containing these high-priced elements.

Furthermore, in the ingredient analysis method and ingredient analysis apparatus in accordance with the present invention, the element to be detected may be bromine. In this case, the substance to be analyzed is, for example, an insulating material in the circuit board to be disposed, and plasma is directly applied with respect to this insulating material. By performing ingredient analysis of printed-circuit boards, etc. as described above, it is possible to separately recover circuit boards to be disposed being in danger of generating dioxin during incineration and those being in no danger.

In the present invention, operability during analysis can be improved by using a configuration wherein lands for analytical use, specially provided for analyzing the ingredients of solder, are formed on printed-circuit boards serving as objects to be inspected. In this case, it is desired that the land for analytical use is a circle more than 0.5 mm in diameter and less than 10 mm in diameter. If the land for analytical use is too small, the positioning of the atmospheric pressure plasma source is difficult. On the other hand, if the land for analytical use is too large, areas not required for circuitry increase on the printed-circuit boards, and this is not economical.

The optical fibers used in the respective embodiments are configured with glass cores having high refractive index and resin clad. In the present invention, plastic optical fibers may be alternatively used. For example, a plastic optical fiber comprising a core made of acrylic resin and a clad made of fluorine resin can be used. By using plastic optical fibers, an ingredient analysis apparatus further excellent in operability and low in cost can be obtained.

In the respective embodiments, the indicator 11 of the information section can be configured with plural emission diodes. With the configuration as such, the level of the emission intensity at a predetermined wavelength can be indicated by the plural diodes. With respect to the substance to be analyzed having low emission intensity, it is possible to repeat ingredient analysis to check again.

Furthermore, in the case of a configuration wherein after ingredient analysis is carried out, depending on the element the presence of which is judged, specific marks particularly assigned to the element are placed on printed-circuit boards, it is possible to securely leave the results of the analysis on the objects to be inspected. The marks can be placed using a method that can be selected from among simple methods, such as painting and sticker attachment.

Furthermore, in the case of a configuration wherein plasma is applied to a portion to be analyzed for a period ranging from several seconds to several minutes to remove stain, such as organic substances and flux, attaching to the surface of the portion to be analyzed, and then emission analysis is carried out, it is also possible to improve detection sensitivity or S/N ratio in the analysis. In this case, the ease of analysis can be raised by using one atmospheric pressure plasma source for stain removing (washing and cleaning) and spectroscopic analysis. In addition, the speed of stain removing can be effectively raised by applying the plasma of a gas containing oxygen or fluorine during stain removing.

As described above, the present invention can attain analysis that can be carried out according to simple operation procedures in a short time with an apparatus compact in size. Moreover, the ingredient analysis method and ingredient analysis apparatus in accordance with the present invention can realize a low-cost analysis. Hence, printed-circuit boards and the like can be separated easily at sites wherein waste, such as used household electric appliances, is processed. Furthermore, in the case that quantitative analysis is nor required, the method in accordance with the present invention is widely applicable as a method for simply making a judgment as to whether a certain element is contained as a primary component or not.

The invention claimed is:

1. An ingredient analysis method comprising the steps of:
   setting the relationship between a wavelength and the emission intensity thereof obtained when plasma is applied to a specific element at atmospheric pressure;
   selecting a specific wavelength having a peak value of the emission intensity on the basis of the relationship set in said step of setting;
   applying said plasma to a substance to be analyzed at atmospheric pressure and measuring the emission intensity of said substance to be analyzed at said wavelength selected in said step of selecting; and
   comparing the emission intensity measured in said step of measuring and the emission intensity at said wavelength of said step of setting and judging the presence or absence of said element in said substance to be analyzed.

2. The ingredient analysis method in accordance with claim 1, wherein when said specific element is lead, when said specific wavelength is 427 nm, 666 nm or 730 nm, and when the emission intensity has an emission peak at said specific wavelength, it is judged that lead is present in said substance to be analyzed.

3. The ingredient analysis method in accordance with claim 1, wherein at said step of measuring, the emission intensity of said substance to be analyzed is measured using arc discharge at a discharge electrode.

4. The ingredient analysis method in accordance with claim 1, wherein at said step of measuring, the emission intensity of said substance to be analyzed is measured at each of a plurality of wavelengths, and at said step of judging, the presence or absence of each of a plurality of elements in said substance to be analyzed is judged.

5. The ingredient analysis method in accordance with claim 1, wherein grinding said substance to be analyzed is preformed at the previous stage of applying, and at said step of grinding, ground powder is dispersed on the surface of said substance to be analyzed.

6. The ingredient analysis method in accordance with claim 1, wherein grinding said substance to be analyzed using a grinding tool is performed at the previous stage of applying, and at said step of appying, said plasma is applied to said substance to be analyzed, disposed on the grinding face of said grinding tool used at said step of grinding, and the emission intensity of said substance to be analyzed is measured, the emission intensity being produced by said plasma.

7. The ingredient analysis method in accordance with claim 1, wherein after the presence or absence of said element is judged at said step of judging, sending information to the outside depending on the result of said judgment is performed.

8. The ingredient analysis method in accordance with claim 1, wherein after the presence or absence of said element is judged at said step of judging, placing specific marks on said substance to be analyzed depending on the result of said judgment is performed.

9. The ingredient analysis method in accordance with claim 1, wherein removing stain from the surface of said substance to be analyzed by applying said plasma to said substance to be analyzed is performed at the previous stage of applying.

10. An ingredient analysis apparatus comprising:
    a sample table on which a substance to be analyzed is placed;
    a discharge electrode having a gas passage formed therein;
    a gas supplying section for supplying gas to said discharge electrode;
    power source for supplying power to said discharge electrode;
    a light transmission section, formed of a light transmission material and having an emission input section disposed near plasma generated between said discharge electrode and said substance to be analyzed, for transmitting light from said substance to be analyzed, said light being generated by plasma irradiation;
    a filter for allowing only the light having a specific wavelength in the light from said light transmission section to pass through; and a controller for measuring the emission intensity of the light having passed through said filter and for judging the presence or absence of a specific element in said substance to be analyzed.

11. The ingredient analysis apparatus in accordance with claim 10, wherein when said specific element is lead, when said specific wavelength is 427 nm, 666 nm or 730 nm, and when the emission intensity has an emission peak at said specific wavelength, said controller judges that lead is present in said substance to be analyzed and stores data concerned.

12. The ingredient analysis apparatus in accordance with claim 10, wherein said discharge electrode is an electrode to which high frequency power is supplied from said power source, and a dielectric substance is formed at the tip of said discharge electrode so as to be opposed to said plasma.

13. The ingredient analysis apparatus in accordance with claim 10, wherein said light transmission section is configured so that the light from said substance to be analyzed enters each of a plurality of filters having different transmittable wavelengths, the emission intensity of the light having passed through each of said filters is measured by said controller, and the presence or absence of each of a plurality of elements to be detected in said substance to be analyzed is detected.

14. The ingredient analysis apparatus in accordance with claim 10, wherein said light transmission section formed of a light transmission material is provided on the external circumference face of said discharge electrode, an emission input section formed of a light transmission material is formed at the tip of said discharge electrode so as to be opposed to said plasma, and the light from said emission input section enters said filter via said light transmission section.

15. The ingredient analysis apparatus in accordance with claim 10, wherein a cylindrical light transmission section formed of a light transmission material is provided so as to cover the external circumference face of said discharge electrode, an emission input section formed of a light transmission material is formed at the tip of said discharge electrode so as to be opposed to said plasma, and a grounded conductive section is provided so as to cover the external circumference face of said light transmission section.

16. The ingredient analysis apparatus in accordance with claim 10, wherein said discharge electrode is provided with a spacer so that the tip of said discharge electrode opposed to said plasma has a desired distance to said substance to be analyzed.

17. The ingredient analysis apparatus in accordance with claim 10, wherein the tip of said discharge electrode opposed to said plasma is provided with a switch, and said switch is made contact with said substance to be analyzed at the time of inspection, thereby to operate analysis processing.

18. The ingredient analysis apparatus in accordance with claim 10, wherein an exhaust passage is provided externally with said discharge electrode so as to be formed integrally.

19. The ingredient analysis apparatus in accordance with claim 10, wherein the tip of said discharge electrode opposed to said plasma is provided with a monitor section having a mirror, a lens and a photodetector.

20. The ingredient analysis apparatus in accordance with claim 10, further comprising informing means, wherein after the presence or absence of said element is judged by said controller, said informing means sends information to the outside depending on the result of said judgment.

* * * * *